US012089906B1

(12) United States Patent
Whitney et al.

(10) Patent No.: US 12,089,906 B1
(45) Date of Patent: Sep. 17, 2024

(54) SYSTEMS AND METHODS FOR REMOTELY CONTROLLING ROBOTIC SURGERY

(71) Applicant: Sovato Health, Inc., Huntington Beach, CA (US)

(72) Inventors: Blair Whitney, Santa Barbara, CA (US); Steven Butner, Santa Barbara, CA (US); Tyler Grotenhuis, Santa Barbara, CA (US); Yulun Wang, Santa Barbara, CA (US); Daniel Haskell, Santa Barbara, CA (US)

(73) Assignee: Sovato Health, Inc., Huntington Beach, CA (US)

( * ) Notice: Subject to any disclaimer, the term of this patent is extended or adjusted under 35 U.S.C. 154(b) by 0 days.

(21) Appl. No.: 18/488,843

(22) Filed: Oct. 17, 2023

Related U.S. Application Data

(60) Provisional application No. 63/585,876, filed on Sep. 27, 2023.

(51) Int. Cl.
*A61B 34/35* (2016.01)
*A61B 90/00* (2016.01)
*G16H 40/67* (2018.01)

(52) U.S. Cl.
CPC .............. *A61B 34/35* (2016.02); *A61B 90/37* (2016.02); *G16H 40/67* (2018.01)

(58) Field of Classification Search
CPC ......... A61B 34/35; A61B 90/37; G16H 40/67
See application file for complete search history.

(56) References Cited

U.S. PATENT DOCUMENTS

| | | |
|---|---|---|
| 7,158,859 B2 | 1/2007 | Wang et al. |
| 7,158,860 B2 | 1/2007 | Wang et al. |
| 7,161,322 B2 | 1/2007 | Wang et al. |
| 7,171,286 B2 | 1/2007 | Wang et al. |
| 7,222,000 B2 | 5/2007 | Wang et al. |
| 7,262,573 B2 | 8/2007 | Wang et al. |
| 7,761,185 B2 | 7/2010 | Wang et al. |
| 7,769,492 B2 | 8/2010 | Wang et al. |
| 8,116,910 B2 | 2/2012 | Walters et al. |
| 9,610,685 B2 | 4/2017 | Wang et al. |
| 9,616,576 B2 | 4/2017 | Roe et al. |
| 10,241,507 B2 | 3/2019 | Wang et al. |

(Continued)

OTHER PUBLICATIONS

Ghodoussi et al., "Robotic Surgery—The Transatlantic Case", Proceedings of the 2002 IEEE International Conference on Robotics & Automation, Washington, DC, May 2002, pp. 1882-1888.

(Continued)

*Primary Examiner* — John R Downey
(74) *Attorney, Agent, or Firm* — Knobbe Martens Olson & Bear, LLP

(57) ABSTRACT

Approaches for remotely controlling a robotic surgery system located at a patient-side location are disclosed. Disclosed approaches reduce transmission delay and ensure reliable transmission for controlling a robotic surgery system from a remote location, which may be in a different city, state, or country. For surgeons, remote surgery facilitates optimal utilization of their time and provides access to a sufficient volume of patients to perfect their skills. For patients, remote surgery creates ample access to the right surgeon and the right care at an affordable price, decreases the need for travel, and reduces delayed care.

16 Claims, 9 Drawing Sheets

(56) References Cited

U.S. PATENT DOCUMENTS

| | | | |
|---|---|---|---|
| 10,259,119 B2 | 4/2019 | Wang et al. | |
| 10,343,283 B2* | 7/2019 | Pinter | H04M 1/72415 |
| 10,493,631 B2 | 12/2019 | Wang et al. | |
| 10,582,259 B2 | 3/2020 | Enke et al. | |
| 10,764,339 B2 | 9/2020 | Pinter et al. | |
| 10,769,739 B2 | 9/2020 | Southard et al. | |
| 10,808,882 B2 | 10/2020 | Wang et al. | |
| 10,871,889 B2* | 12/2020 | Ballantyne | G06F 3/1454 |
| 10,875,183 B2 | 12/2020 | Herzog et al. | |
| 10,878,960 B2 | 12/2020 | Wang et al. | |
| 10,882,180 B2 | 1/2021 | Wright et al. | |
| 10,882,190 B2* | 1/2021 | Wang | G05D 1/0272 |
| 10,887,545 B2 | 1/2021 | Stuart et al. | |
| 10,889,000 B2 | 1/2021 | Wang et al. | |
| 10,911,715 B2 | 2/2021 | Wang et al. | |
| 10,969,766 B2 | 4/2021 | Wang et al. | |
| 10,984,916 B2 | 4/2021 | Celmins et al. | |
| 11,123,876 B2 | 9/2021 | Peterson | |
| 11,154,981 B2 | 10/2021 | Hanrahan et al. | |
| 11,205,510 B2 | 12/2021 | Ross et al. | |
| 11,389,962 B2 | 7/2022 | Pinter et al. | |
| 11,468,983 B2 | 10/2022 | Wang et al. | |
| 11,482,326 B2 | 10/2022 | Kahn | |
| 11,628,571 B2 | 4/2023 | Pinter et al. | |
| 11,636,944 B2 | 4/2023 | Hanrahan et al. | |
| 2003/0071893 A1 | 4/2003 | Miller et al. | |
| 2007/0130457 A1* | 6/2007 | Kamat | H04L 63/0281 |
| | | | 713/151 |
| 2009/0326979 A1* | 12/2009 | Ryan | G16H 80/00 |
| | | | 348/E7.083 |
| 2010/0076600 A1 | 3/2010 | Cross | |
| 2011/0187875 A1 | 8/2011 | Sanchez et al. | |
| 2011/0190930 A1 | 8/2011 | Hanrahan et al. | |
| 2011/0213210 A1* | 9/2011 | Temby | G16H 40/67 |
| | | | 348/14.02 |
| 2012/0191464 A1 | 7/2012 | Stuart et al. | |
| 2013/0293373 A1* | 11/2013 | Gegner | G16H 40/67 |
| | | | 340/527 |
| 2015/0092037 A1 | 4/2015 | Wang et al. | |
| 2016/0188693 A1 | 6/2016 | Peters | |
| 2016/0368146 A1* | 12/2016 | Mangaser | G05D 1/0022 |
| 2017/0105010 A1 | 4/2017 | Wu et al. | |
| 2017/0300654 A1* | 10/2017 | Stein | H04L 69/40 |
| 2018/0250086 A1* | 9/2018 | Grubbs | A61B 34/35 |
| 2018/0257233 A1 | 9/2018 | Wright et al. | |
| 2018/0297210 A1* | 10/2018 | Peterson | H04N 19/37 |
| 2018/0308565 A1 | 10/2018 | Pinter et al. | |
| 2018/0322255 A1* | 11/2018 | Connell, II | G16H 50/20 |
| 2019/0009360 A1* | 1/2019 | Aoki | B23K 26/06 |
| 2019/0088364 A1 | 3/2019 | Wang et al. | |
| 2019/0134818 A1 | 5/2019 | Mangaser et al. | |
| 2019/0174322 A1* | 6/2019 | Deviprasad | H04L 41/0853 |
| 2019/0188992 A1* | 6/2019 | Bodurka | G08B 25/004 |
| 2019/0326015 A1* | 10/2019 | Cannell | G16H 40/20 |
| 2019/0374298 A1 | 12/2019 | Allen, IV | |
| 2020/0066414 A1* | 2/2020 | Neff | H04L 12/1818 |
| 2020/0169856 A1* | 5/2020 | Yang | H04L 67/1008 |
| 2020/0197116 A1 | 6/2020 | Linebarger | |
| 2020/0203000 A1* | 6/2020 | Neville | H04L 65/80 |
| 2020/0222129 A1* | 7/2020 | Gomez | A61B 34/30 |
| 2020/0237224 A1 | 7/2020 | Sanchez et al. | |
| 2020/0360607 A1* | 11/2020 | Pfeiffer | G16H 20/17 |
| 2020/0383734 A1 | 12/2020 | Dahdouh | |
| 2021/0145526 A1* | 5/2021 | Robinson | A61B 34/35 |
| 2021/0178597 A1 | 6/2021 | Pinter | |
| 2021/0220064 A1* | 7/2021 | Kottenstette | G16H 40/63 |
| 2021/0298845 A1 | 9/2021 | Freiin von Kapri | |
| 2022/0284994 A1* | 9/2022 | Ellis | H04L 67/55 |
| 2022/0331054 A1* | 10/2022 | Kimball | A61B 17/07207 |
| 2023/0020577 A1 | 1/2023 | Kerver | |
| 2023/0128665 A1* | 4/2023 | Kottenstette | A61B 34/37 |
| | | | 700/245 |
| 2023/0157762 A1 | 5/2023 | Braido | |
| 2023/0360336 A1 | 11/2023 | Weibel | |
| 2023/0364290 A1* | 11/2023 | Hamidi | G16H 20/40 |
| 2023/0390009 A1 | 12/2023 | Scholan | |

OTHER PUBLICATIONS

Gu et al., "Robotic surgery in China", The Innovation, Sep. 11, 2023, vol. 4, No. 5, in 2 pages.

Harvard Business Review, Can Remote Surgeries Digitally Transform Operating Rooms?, https://hbr.org/podcast/2023/09/can-remote-surgeries-digitally-transform-operating-rooms, Sep. 12, 2023, Downloaded Nov. 15, 2023, in 15 pages.

Karl Storz Endoscopy-America, "Agreements/contracts: Karl Storz, InTouch to develop new surgical mentoring tool", www.bioworld.com/articles/443201, Mar. 18, 2009, in 2 pages.

McCamant, SSII: Amid Aggressive MedTech M&A, Could Robotic Surgery Company Find Itself in Someone's Crosshairs?, https://www.moneyshow.com/articles/dailyguru-61587/ssii-amid-aggressive-medtech-m-and-a-could-the-robotic-surgery-company-find-itself-in-someones-crosshairs/#, Sep. 19, 2023, Downloaded from the Internet Nov. 15, 2023, in 2 pages.

Smith, Craig S., "AI Poised to Transform Video-Compression Landscape, Apple's WaveOne purchase heralds a new era in smart-streaming of AR and video", IEEE Spectrum, Apr. 12, 2023, in 6 pages.

Suermann, Amelia, "Data Reveal the Details about the Surgeon Workforce Shortage", The Bulletin, Feb. 4, 2022, in 5 pages.

Surgical Robotics Technology, "Monogram Orthopaedics Selects RTI Connext Anywhere as the Connectivity Software Solution", https://www.surgicalroboticstechnology.com/news/monogram-orthopaedics-selects-rti-connext-anywhere-as-the-connectivity-software-solution/, May 24, 2023, Downloaded Nov. 15, 2023, in 6 pages.

Teladoc Health, Teladoc HealthTM Care Location App ModuleTM User Guide, 2021, in 71 pages.

Teladoc Health, "Teladoc HealthTM Lite V2 & V3 Under Guide", 2021, in 65 pages.

Whooley, Sean, "FDA clears Insight Medbotics' MRI-compatible surgical robot", https://www.massdevice.com/fda-clears-insight-medbotics-mri-compatible-surgical-robot/, Sep. 13, 2023, Downloaded from the Internet Nov. 15, 2023, in 5 pages.

Whooley, Sean, "Quantum Surigcal wins CE mark to treat lung tumors with its surgical robot", https://www.massdevice.com/quantum-surgical-lung-tumors-surgical-robot/, Sep. 11, 2023, Downloaded from the Internet Nov. 15, 2023, in 4 pages.

Woods, Rae, "The State of the Healthcare Industry Heading Into 2024", Advisory Board, 2023, in 36 pages.

youtube.com, "InTouch Provider Access", https://www.youtube.com/watch?v=By9azc1zz3k, Downloaded Nov. 21, 2023, in 2 pages.

youtube.com, "Monogram Makes Orthopedic History! Fully Remote Robotic Surgical Demo", https://www.youtube.com/watch?v=j0OQk8mT-bs, Mar. 10, 2023, Downloaded Nov. 16, 2023, in 3 pages.

\* cited by examiner

SYSTEMS AND METHODS FOR REMOTELY CONTROLLING ROBOTIC SURGERY

CROSS REFERENCE TO RELATED APPLICATIONS

This application claims priority to U.S. Provisional Patent Application No. 63/585,876, filed on Sep. 27, 2023, which is incorporated by reference in its entirety. Any and all applications for which a foreign or domestic priority claim is identified in the Application Data Sheet as filed with the present application are hereby incorporated by reference under 37 CFR 1.57.

TECHNICAL FIELD

This disclosure relates generally to robotic surgery and more particularly to remotely controlling a robotic surgery system.

DESCRIPTION OF RELATED ART

Robot-assisted surgery systems are generally available and have been developed to operate efficiently and safely. A robotic surgery system typically includes robotically actuable surgical instruments that may be inserted within the patient's body to perform a surgical procedure at a surgical site. The robotic surgery system is typically controlled by a surgeon via a surgeon input console, which is connected to the robotic surgery system via a control cable. The surgeon input console includes input devices that are grasped by the surgeon's hands and moved to generate signals for activating the surgical instruments to perform surgical operations at the surgical site. Signals are transmitted over the control cable to the robotic surgery system, which interprets the signals and generates control signals that cause the instruments to be actuated to perform surgical operations.

SUMMARY

Disclosed systems, apparatuses, and methods enable remotely controlling a robotic surgery system located at a patient-side location. Disclosed approaches reduce transmission delay and ensure reliable transmission for controlling a robotic surgery system from a remote location, which may be in a different city, state, or country. For surgeons, advantageously, remote surgery facilitates optimal utilization of their time and provides access to a sufficient volume of patients to perfect their skills. For patients, advantageously, remote surgery creates ample access to the right surgeon and the right care at an affordable price, decreases the need for travel, and reduces delayed care.

Other aspects and features will become apparent to those ordinarily skilled in the art upon review of the following description of specific disclosed implementations in conjunction with the accompanying figures.

BRIEF DESCRIPTION OF THE DRAWINGS

In drawings which illustrate disclosed implementations.

DETAILED DESCRIPTION

Figure 1:
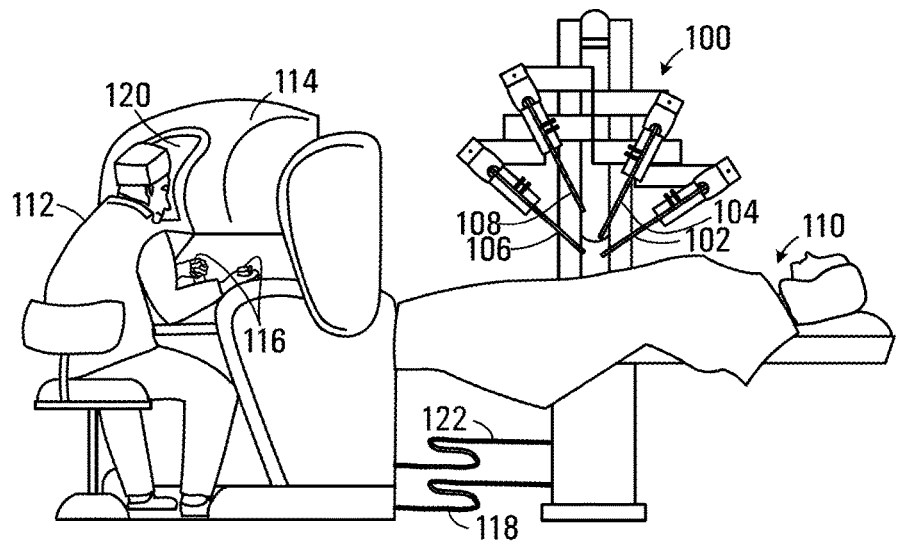
FIG. 1 is perspective view of a robotic surgery system.

Referring to FIG. 1, a robotic surgery system is shown generally at 100. The robotic surgery system 100 includes a plurality of robotically actuable surgical instruments 102-108 positioned on one or more robotic arms. At least one of the instruments 102-108 will generally be configured as an in-patient imaging system (such as, a camera, fluoroscopy system, radiography system, computer tomography (CT) system, ultrasound system, magnetic resonance imaging (MRI) system, or the like), which is inserted the body of the patient to generate images of anatomical structures and the surgical instruments 102-108 at a surgical site within the body of a patient 110. The remaining instruments may be configured to include an end effector that performs a specific surgical function (such as, forceps/graspers, needle drivers, scissors, electrocautery hooks, staplers, clip appliers, removers, etc.). The system 100 is controlled by a surgeon 112 via a surgeon input console 114, which is connected to the robotic surgery system 100 via a control cable 118. The surgeon input console 114 includes input devices (not shown) including handles 116 that are grasped by the surgeon's left and right hands and moved within an input device workspace or otherwise actuated to generate input signals. The input devices include encoders that transform positions and orientations of the handles 116 into input signal data representing the surgeon input. The input signals may thus be used for activating the plurality of surgical instruments 102-108 to perform surgical operations at the surgical site. The input signals are transmitted over the control cable 118 to the system 100, which interprets the signals and generates control signals that cause the instruments 102-108 to be actuated to move and perform other surgical operations. The input signals will generally be output by the input devices on the surgeon input console 114 as data signals representing the inputs to the console provided by the surgeon 112. For example, the surgeon input console 114 may generate input signals in the form of motion control signals that represent instantaneous positions of the handles 116 of the input devices within an input device workspace. The data signals are transmitted over the control cable 118, which is generally a wired connection between the surgeon input console 114 and the robotic surgery system 100. The wired connection ensures negligible transmission delay such that operations of the surgical instruments 102-108 caused by the surgeon will be effected by the system 100 with negligible delay. The control cable 118 may be implemented using any of a variety of different data transmission technologies such as Ethernet or Controller Area Network (CAN bus) protocol.

Additional input signals may also be generated at the surgeon input console 114. For example, the handles 116 may include other controls (not shown) that may be used to generate actuation signals that actuate operations at the surgical instruments 102-108, such as opening or closing a surgical scissor or forceps. The surgeon input console 114 may also include one or more foot pedals (not shown) that may be actuated by the surgeon to initiate various other operations. For example, a foot pedal may be configured to generate a clutch signal for temporarily decoupling the surgical instruments 102-108. A foot pedal may also be configured to initiate delivery of energy, such as generate electrocautery signals for initiating delivery of an electrocauterization current to an instrument, to cut, cauterize, or coagulate tissue (which can involve resection of tissue, vaporization of tissue, or coagulation of tissue). Delivery of energy can include delivery of ultrasonic energy (such as, with a harmonic scalpel instrument), delivery of electric energy (such as, with an electrocautery instrument), delivery of laser energy (such as, with a cautery instrument), delivery of radio frequency energy (such as, with a cautery instrument), or the like. These other input signals also need to be delivered to the robotic surgery system 100 to initiate their respective operations. Additionally, the robotic surgery system 100 may generate event-oriented notifications such as notifications of error conditions that must be communicated to the surgeon input console 114 to update the surgeon 112. Event-oriented messages may be time-sensitive, but are not necessarily synchronous.

The surgeon input console 114 also includes a display 120 for displaying images generated by the in-patient imaging system. The in-patient imaging system would generally be implemented as a high-resolution imaging system (such as, a video camera) that generates a stream of image frames. In some instances, the imaging system may generate images from differing perspectives that convey three-dimensional information and the display 120 may be configured as a stereoscopic display. The display signals generated by the imaging system are transmitted over an image transmission cable 122 back to the surgeon input console 114 for driving the display 120. The image transmission cable 122 is generally selected to ensure that the image frames are delivered to the display in near real-time so that the surgeon 112 does not perceive any delay between their hand movements and movements of the surgical instruments 102-108 represented on the display. In some implementations, the input signals and display signals may both be transmitted over a single shared cable or bus.

The robotic surgery system 100 may be housed within a sterile operating room that forms part of an operating suite. The surgeon or another surgeon aided by a perioperative nurse may make the necessary incisions and insert the instruments 102-108. The surgeon input console 114 may be housed in a portion of the operating suite that is separated from the operating room so that the surgeon operating the input console need not wear surgical gloves while manipulating the controls of the input console. The cables 118 and 122 would generally extend through a port in a wall between the surgeon input console 114 and the robotic surgery system 100. In cases where another surgeon performs the incisions in the body of the patient 110, the operating surgeon may not need to complete the full process of scrubbing, gowning, and gloving before the operation. In this situation, the surgeon input console 114 however remains in a direct wired connection with the robotic surgery system 100 via the cables 118 and 122. The direct wired connection ensures that the robotic surgery system 100 is able to rapidly respond to the surgeon's inputs provided at the surgeon input console 114 and the display 120 displays images of the surgical site with a negligible delay that is virtually unnoticeable to the surgeon.

Overview of Remotely Controlling Robotic Surgery

One of the main problems in the healthcare industry is the lack of surgeons and underutilization of surgeons. On one hand, there is a lack of high-quality surgeons. For instance, a 2022 article by the American College of Surgeons concludes that there is an acute ongoing shortage of surgeons available in the United States to serve the patient population. The shortage of high-quality surgical care is particularly severe in rural areas. In addition, surgeons in many geographical areas may not have access to a sufficient volume of patients to perfect their surgical skills because the population is not evenly distributed, thus creating a lack of surgical volume in such areas. On the other hand, currently there are severe inefficiencies with utilizing the time of surgeons. Surgeons are required to travel between different hospitals, some of which may be located in difficult to reach places or between different operating rooms in a single hospital. Moreover, surgeons are required to wait for patients and operating rooms to be prepared for surgery. This results in a serious underutilization of surgeons' time. There are many advantages in allowing surgeons to control robotic surgery systems (such as, the system 100) from remote locations in order to increase efficiency and improve patient care. For surgeons, remote surgery facilitates optimal utilization of their time and provides access to a sufficient volume of patients to perfect their skills. For patients, remote surgery creates ample access to the right surgeon and the right care at an affordable price, decreases the need for travel, and decreases delayed care. However, there are a number of challenges with designing a system that would allow remotely controlling robotic surgery systems. These include transmission delay and reliability of transmission.

Figure 2:
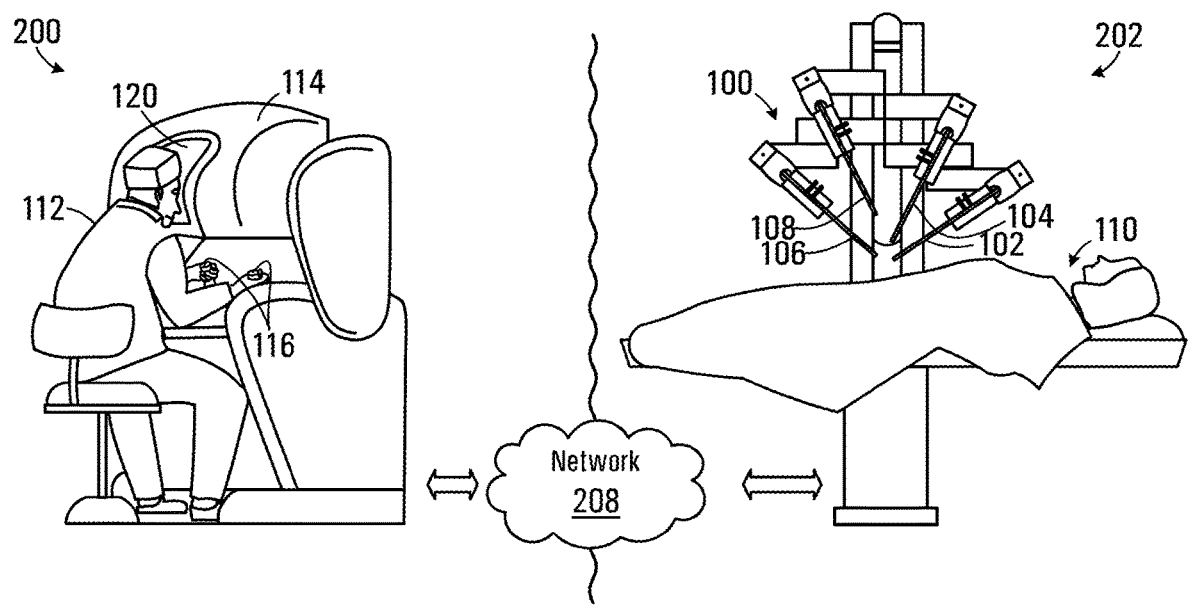
FIG. 2 is perspective view of a robotic surgery system.

Referring to FIG. 2, the surgeon input console 114 is disposed at a surgeon-side location 200 and the robotic surgery system 100 shown in FIG. 1 is disposed at a patient-side location 202. The surgeon-side location 200 is remote from the patient-side location 202 to an extent where a directly wired connection between the robotic surgery system 100 and the surgeon input console 114 is no longer possible. Advantageously, the surgeon-side location 200 may be in another building or even another city, state, or country. In this example, communications are conducted between the surgeon-side location 200 and the patient-side location 202 via a network 208 and there is no direct wired connection between the surgeon input console 114 and the robotic surgery system 100.

Figure 3:
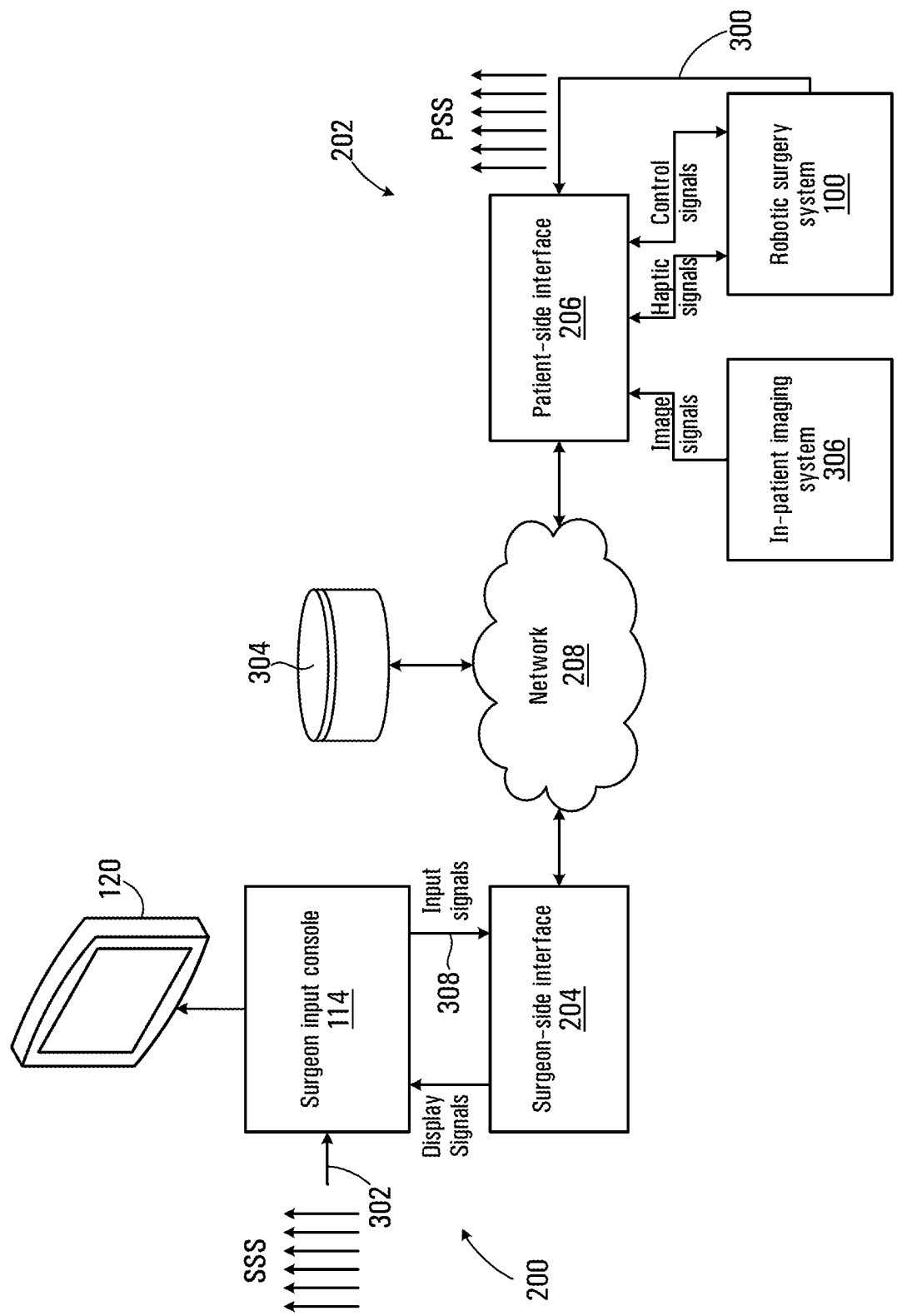
FIG. 3 is a block diagram of components of the robotic surgery system of FIG. 2.

Referring to FIG. 3, communication between the surgeon-side location 200 and patient-side location 202 are conducted via a surgeon-side interface 204 and a patient-side interface 206, which are shown schematically in FIG. 3. The surgeon-side interface 204 is connected to receive input signals from the surgeon input console 114. For example, the surgeon input console 114 may generate a stream of motion input signals 308 that represent the instantaneous position of the handles 116 within an input console workspace. Motion input signals can represent a desired movement (including position and velocity) of an instrument in the input console workspace. These motion input signals will generally be transformed via kinematic processing into signals representing desired positions and orientations of the joints of the instruments 102-108 within a surgical workspace of the robotic surgery system 100. In some instances, kinematic processing translates the position and movement of the handles 116 within the input console workspace into the position and movement of joints of the instruments 102-108. The translation can be performed by transforming the position and orientation of the handles 116 in the Cartesian coordinate system to the coordinates of the joints of the instruments 102-108 in the surgical workspace and vice versa. Other processing functions may then be used to transform these kinematically derived instrument joint positions into drive signals for actuating various actuators, such as motor servos, that cause movement of the instruments 102-108 within the surgical workspace. In the system shown in FIG. 1, the kinematic and other processing may be implemented within the surgeon input console 114 or the within robotic surgery system 100. In the implementation of FIG. 3, the input signals 308 can be picked up directly from the input devices of the surgeon input console 114 and before any kinematic or other processing has been performed. For some robotic surgery system 100, the input signals are generated by the input devices of the surgeon input console 114 at a relatively low frequency (or rate of change), for example about 200 Hz or every 5 milliseconds or about 30 Hz or less. The input signals 308 thus require a relatively low bandwidth or data rate for transmission. In contrast, post-kinematics and other processing signals may have a significantly higher frequency (or rate of change). As an example, in some robotic surgery systems the servo rate at the motor controller may be in the region of about 10 kHz or more, which may require a significantly higher bandwidth or data rate for transmission than the motion input signals generated at the input device.

In general, remotely controlling a robotic surgery system can be achieved by transmitting from the surgeon-side interface 204 to the patient-side interface 206 a complete set of signals that control the instruments 102-108 (which include at least one imaging system). To reduce delay and guarantee reliability of the transmission, such set of signals can include signals having the lowest frequency (or rate of change) among a plurality of available signals. As described above, input signals 308 can be transmitted from the surgeon-side interface 204 to the patient-side interface 206, rather than signals generated as a result of kinematic processing that generates signals representing desired coordinates of the joints of the instruments 102-108 in the surgical workspace associated with the robotic surgery system 100 or the drive signals (such as, torque) for actuating the motors of the instruments 102-108. In some cases, the surgeon-side interface 204 can select input signals 308 for transmission from the plurality of available signals, which can include signals generated as a result of kinematic processing and the drive signals.

In certain implementations, one or more signals generated as a result of kinematic processing may be transmitted by the surgeon-side interface 204 to the patient-side interface 206. These signals can be transmitted along the input signals 308.

The surgeon-side interface 204 is in communication with the patient-side interface 206 over the network 208. The patient-side interface 206 is in communication with the robotic surgery system 100 for receiving and delivering control signals to the robotic surgery system. The patient-side location 202 also includes an in-patient imaging system 306, which generates images of the surgical site within the patient. As described above, one of the surgical instruments 102-108 may be configured to generate the in-patient images or a separate imaging system may be employed. The in-patient imaging system 306 generates data representing image frames, which is encoded into an image data stream by the patient-side-interface 206 and transmitted over the network 208 to the surgeon-side interface 204. The surgeon-side interface 204 receives and decodes the image data stream to recover the image frame data, which is sent via the surgeon input console 114 to the display 120 associated with the surgeon input console 114. The surgeon 112 is able to view the surgical site on the display 120 and cause movements of the handles 116 of the surgeon input console 114, which are encoded by the input devices and delivered as input signals to the patient-side interface 206.

The robotic surgery system 100 may be additionally configured to generate haptic feedback and/or force feedback signals. In robotic surgery, haptic feedback signals may be generated to alert the surgeon 112 when an attempt is made to move one of the instruments 102-108 against an instrument movement boundary or other impediment to motion. Haptic signals may also be generated when two of the instruments 102-108 are moved toward a collision condition. These haptic signals are generally used to deliver haptic feedback via the handles 116 of surgeon input console 114 that alert the surgeon 112 to the condition. Additionally, some robotic systems may also be configured to generate force feedback signals that can be used to deliver force feedback to the surgeon via the input console 114. The force feedback may serve to indicate that the surgeon 112 is attempting to move one of the instruments 102-108 against a limitation such as human tissue or an organ. In some implementations the patient-side interface 206 may be configured to receive the haptic or force feedback signals and transmit the signals back to the surgeon-side interface 204 for delivery to the surgeon input console 114.

The network 208 may be provided as a connection to the internet. In some cases, the network 208 may be a dedicated network such as a point-to-point fiber or a specially-conditioned and monitored network that aims to reduce transmission delay and increase reliability and stability. The surgeon-side interface 204 is in communication with the robotic surgery system 100 at the patient-side location 202 via the network 208.

System for Remotely Controlling Robotic Surgery

Figure 4A:
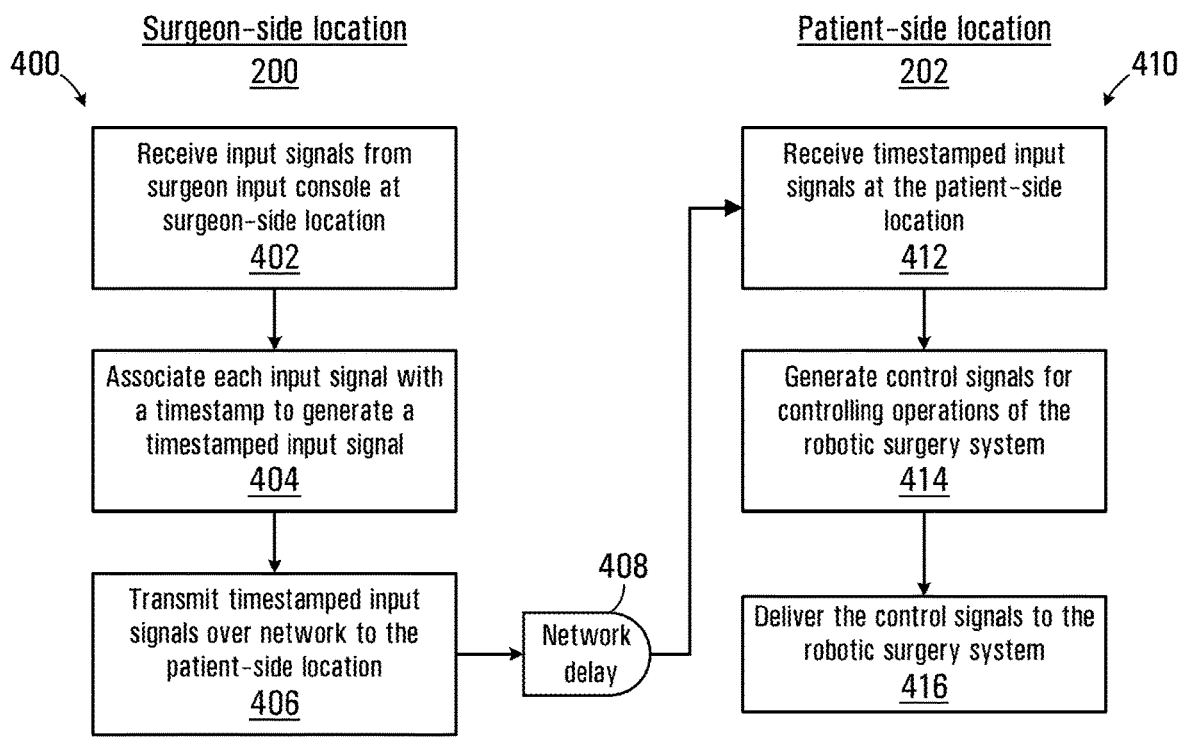
FIG. 4A is a flowchart depicting functions performed by a surgeon-side interface and a patient-side interface.

Referring to FIG. 4A, a flowchart depicting functions performed by the surgeon-side interface 204 for generating temporally ordered input signals (such as, timestamped input signals) is shown generally at 400. At block 402, the input signals are received from the surgeon input console 114. At block 404, each input signal is associated with a timestamp to generate a timestamped input signal. As an example, each motion input signal may include a number of bytes of data representing an instantaneous position of the handles 116 of the surgeon input console 114 and the timestamp may be embedded in or appended to the input bytes. Other input signals such as the actuation signals, clutch signals, and energy delivery signals (such as, electrocautery signals) may be similarly timestamped. At block 406 the timestamped input signals are transmitted over the network 208 to the patient-side location 202. In some instances, since the input signals may typically be represented in less than 10 bytes of data, several timestamped input signals may be combined for more efficient transmission over the network 208. In some implementations, the transmitted data may be encrypted prior to transmission. The transmission of the timestamped input signals will generally be subject to a network transmission delay 408 that will vary based on the distance of transmission, the quality of the network, and various other factors that affect the transmission time.

A flowchart depicting functions performed by the patient-side interface 206 for delivering control signals to the robotic surgery system 100 is shown generally at 410. At block 412 the timestamped input signals are received at the patient-side location 202. If the transmission was encrypted at the surgeon-side interface 204, data decryption is performed on the received data. In some cases, one or more of the timestamped input signals may have been received in an order that differs from the transmission order at block 406. In such cases the input signals may be re-ordered by the patient-side interface 206 on receipt at block 412. Additionally, if the received input signals include more than one timestamped input signal, the data may be processed to separate the individual timestamped input signals.

At block 414, control signals are generated for controlling operations of the robotic surgery system 100. Each control signal is based on one or more of the timestamped input signals. In some instances, there may be a direct one-to-one correspondence between each timestamped input signal and the resulting control signal. However, in some implementations, more than one input signal may be processed to generate each control signal. At block 416, the control signals are delivered to the robotic surgery system 100 at times based on the timestamp of the respective input signals. As such, the chronological order and timing of the delivery of the control signals to the robotic surgery system 100 will generally correspond to the chronological order and timing of the inputs provided by the surgeon 112 at the surgeon input console 114 on the surgeon-side location 200.

Figure 4B:
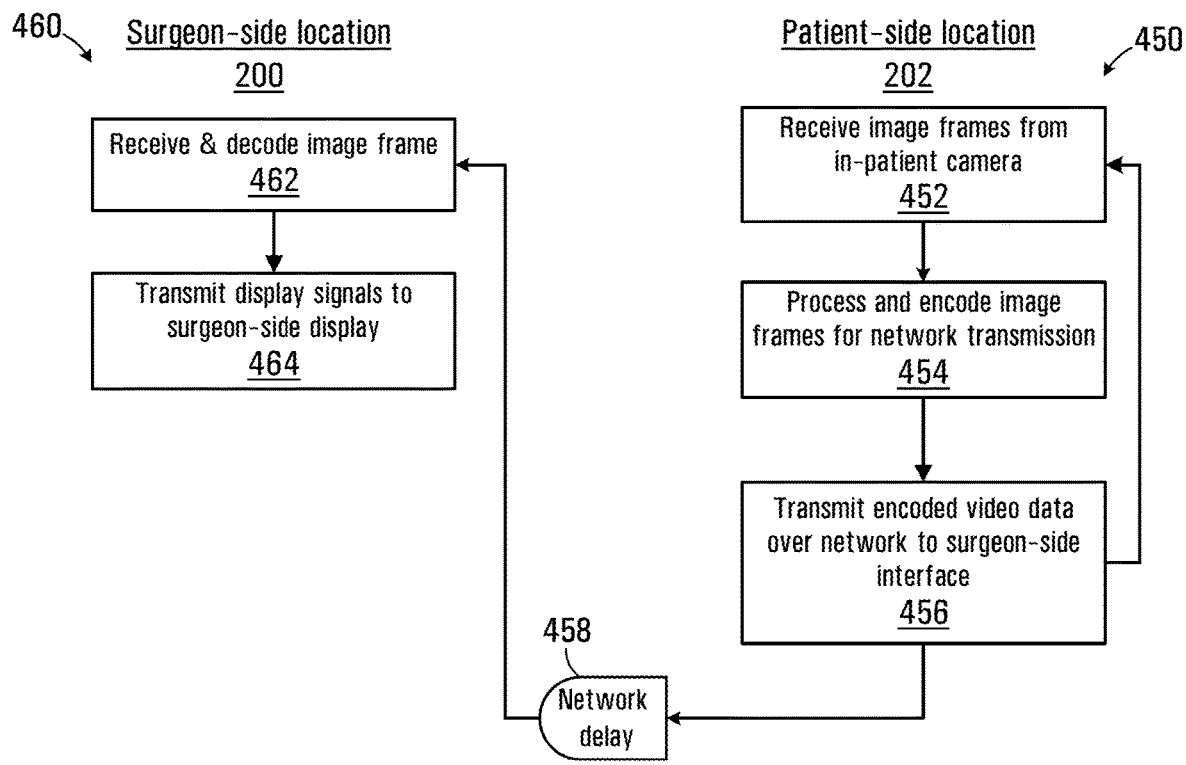
FIG. 4B is a flowchart depicting functions performed by the patient-side interface for transmitting video frame images.

Referring to FIG. 4B, a flowchart depicting functions performed by the patient-side interface 206 for transmitting video frame images generated by the in-patient imaging system 306 to the surgeon-side interface 204 is shown generally at 450. At block 452 one or more image frames are received from the in-patient imaging system 306 at the patient-side interface 206. At block 454 the image frames are encoded and compressed for transmission to the surgeon-side location 200. In some cases, the image frames are encoded by implementing an image codec (such as, a video codec in case of video images) on the patient-side interface 206. Frames may be received from the in-patient imaging system 306 at a frame rate of 30 frames per second (fps) or approximately every 33 msec. The video codec will generally take advantage of portions of successive image frames that are unchanging to compress the video frame images and reduce the size of the video frame images, which facilitates reduced transmission time over the network 208. Advantageously, this can facilitate efficient transmission of video frame images across the network 208.

In some cases, such as for some high-density image frame formats, the time taken to perform the video encoding of the frames may result in an unacceptable delay. Additionally, the in-patient imaging system 306 may be implemented as a stereoscopic camera, which generates images frames from at least two different perspective viewpoints to facilitate generation of a three-dimensional view at the display 120 of the surgeon input console 114. Stereoscopic images will double the amount of image data that needs to be encoded. In some instances, a hardware video codec of may be implemented to reduce the video encoding time. The hardware video codec may include discrete hardware logic or may be implemented using a graphics processing unit (GPU), field-programmable gate array (FPGA) or application-specific integrated circuit (ASIC). As an example, a hardware-based codec may be configured to encode a typical video frame in less than 1 millisecond, while a software-based codec may take about 8 milliseconds for encoding the frame. Added to these delays would be the time taken by a frame grabber to capture each image frame from the in-patient imaging system 306 and the time taken to perform any additional processing on the image data. For example, where the feed from the in-patient imaging system 306 includes two stereo images, the data for the two images may need to be assembled for transmission as a single serial stream prior to encoding.

At block 454, the image frames may also be timestamped as described above for the input signals. The timestamp may be embedded within the video data stream such that a time of receipt from the in-patient imaging system 306 is associated with each frame. Subsequently when the frames are received at the surgeon-side location 200, the timestamps may be used to display the frames at a frame rate that corresponds to the rate of capture by the in-patient imaging system 306.

At block 456 the encoded video frame data is transmitted over the network 208 to the surgeon-side interface 204. Transmission over the network will also have a network delay 458 that will vary based on the distance of transmission, the quality of the network, and various other factors that affect transmission time. The network delay 458 may also vary over time. This time variance is typically known as network jitter and shared networks in particular may exhibit quite considerable network jitter.

In some implementations, smaller portions of one or more video frames can be encoded and transmitted over the network 208 rather than waiting for an entire video frame to be captured and processed. A chunk or slice of lines from a video frame can be captured and encoded. This process can continue for each subsequent slice until the entire frame has been encoded. Advantageously, such slice encoding can reduce encoding latency because encoding can begin immediately after an initial slice has been received. In addition, multiple slices can be encoded in parallel leading to more efficient use of hardware resources and further reduction of encoding latency. Slice encoding can be more resilient to errors (including transmission errors) because any error or corruption of one of the slices would not affect the entire frame and the corrupted slice can be corrected or retransmitted. Bandwidth usage can be smoothed out since encoded slices can be transmitted at regular intervals rather than sending bursts of one or more entire frames.

A process for receiving the encoded video data at the surgeon-side location 200 is shown at 460. At block 462, the encoded video data is received and decoded to recover the original image frame data. As in the case of the patient-side interface 206, a video codec may be implemented as either a hardware of software codec for decoding the received video data. At block 464, appropriately formatted display signals are then generated and transmitted to the display 120 of the surgeon input console 114.

The surgeon 112 will inherently expect to see commanded movements displayed on the display 120 of the surgeon input console 114 within a short period of time (typically about 40 msec). If the round-trip delay related to transmission of the input signals from the surgeon-side interface 204, generation of control signals at the patient-side interface 206, and transmission of the video frames back to the surgeon-side interface is too long, the surgeon 112 will start to notice unpredictability in the commanded movements. The surgeon 112 will likely respond by working more slowly. In previous remote surgery experimentation, it was empirically determined that a round-trip delay of under about 330 msec was deemed comfortable, while delays up to about 1000 msec may be workable, but may be considered by some surgeons to be unsafe.

In the configuration shown in FIG. 3, a data store 304 is included in communication with the network 208. The data store 304 may be used as remote network storage for storing data logs and other information connected with surgical operations performed by the systems shown.

In the configuration shown in FIG. 3, the robotic surgery system 100 generates a patient-side synchronization signal (PSS) 300 that is used at the within the robotic surgery system to synchronize motion signals that are sent to the surgical instruments 102-108. In some instances, the PSS signal may be generated as train of regular periodic clock signal pulses. In some cases, the PSS signal may have an asynchronous component that causes its periodicity to vary by some small amount. The PSS signal is received at the surgeon-side interface 204 for synchronizing functions provided by the surgeon-side interface, as described in more detail below. In some implementations, the PSS signal may have an average frequency of about 200 Hz, which corresponds to about 5 msec between pulses.

The surgeon input console 114 can be configured to generate a surgeon-side synchronization signal (SSS) 302, which may have the same or similar characteristics to the PSS signal. The SSS signal is used to synchronize sampling of the input controls to generate control signals within the surgeon input console 114. While the PSS and SSS signals are decoupled, the SSS signal is generated to have a frequency that corresponds to the average frequency of the PSS signal. This correspondence causes input signals to be generated at about the same rate as the signals will be delivered to the robotic surgery system 100 at block 416 (such as, about every 5 msec).

In the system shown in FIG. 1, a single synchronization signal may be generated in either the robotic surgery system 100 or the surgeon input console 114. If generated in the robotic surgery system 100, the synchronization signal may be communicated via the control cable 118 to the surgeon input console 114. Alternatively, if generated in the surgeon input console 114, the synchronization signal may be communicated via the control cable 118 to the robotic surgery system 100.

In contrast, in the configuration shown in FIG. 2 and FIG. 3, the synchronization signals are separately generated at the patient-side location 202 and surgeon-side location 200. This configuration provides the necessary synchronization for both surgeon input console 114 and robotic surgery system 100 and avoids any need to transmit the synchronization signal over the network 208.

Handling of event-oriented notifications, which are not necessarily synchronous, may be similar to the input signals in that each event-oriented notification would be timestamped. Event-oriented notifications can include embedded status and timeout data. The status indicates whether the event status is unknown, pending, or already updated. The timeout time may be expressed in terms of a video image frame number, indicating that the event-oriented notification must be delivered before a certain image frame has been transmitted to the surgeon-side interface 204. At the surgeon-side location 200 the surgeon-side interface 204 keeps a separate record of the event-oriented notifications and updates the status when delivered to the surgeon input console 114. If the status remains unknown or pending beyond the timeout value, the surgeon input console 114 raises a severe error notification. Depending on the specific error condition, operation of the robotic surgery system 100 may be halted or operations may continue.

The robotic surgery system 100 may from time-to-time generate event-oriented notifications at the patient-side location. Each event-oriented notification at the patient-side location 202 may be processed to generate a notification record including a timestamp indicating a time at which the event-oriented notification was generated, status information including information indicating a processing status of the event-oriented notification, and timeout information including information indicating an expiry time by which the event-oriented notification should be processed. These notification records are then transmitted to the surgeon-side location 200. At the surgeon-side location 200, each notification record is received and accumulated for processing. When the status in the notification record indicates that the notification record has not yet been communicated to the surgeon input console and the expiry time in the timeout information exceeds the current time at the surgeon-side location 200 (for instance, as maintained by the surgeon-side interface 204), an alert is generated. When the status indicates that the notification record has not yet been communicated to the surgeon input console and the expiry time does not yet exceed the current time at the surgeon-side location 200, a notification message is generated and communicated to the surgeon input console. The status in the notification record is then changed to indicate that the notification record has been processed.

While certain examples of temporal ordering have been described in the context of using timestamps, other approaches can be used, such as assigning sequence numbers (which can be assigned in a sequential order).

While certain examples of encoding and decoding images have been described in the context of video encoding and decoding, image codecs can be used similarly for encoding and decoding other types of images, such as fluoroscopy images, radiography images, CT images, ultrasound images, or MRI images.

Surgeon-Side Interface

Figure 5A:
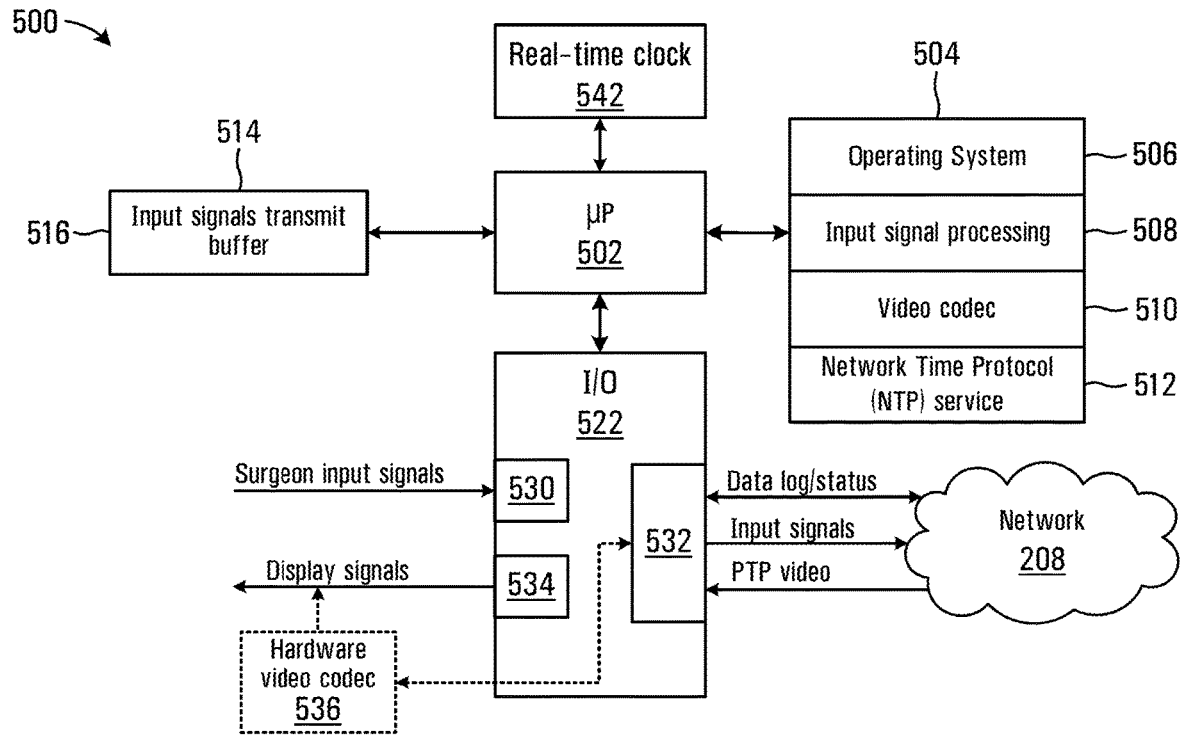
FIG. 5A is a block diagram of a processing circuitry for implementing the surgeon-side interface.

The surgeon-side interface 204 may be implemented using the processing circuitry shown generally at 500 in FIG. 5A. Referring to FIG. 5A, the surgeon-side processing circuitry 500 includes a controller or processor 502, a program memory 504, a variable memory 514, and an input output port (I/O) 522, all of which are in communication with the processor 502.

Program codes for directing the processor 502 to carry out various functions are stored in the program memory 504, which may be implemented as a random-access memory (RAM) and/or a hard disk drive (HDD), or a combination thereof. The program memory includes operating system program codes 506 for directing the processor 502 to provide operating system functions, a input signal processing program codes 508 for directing the processor to provide input signal processing functions, video codec program codes 510 for directing the processor to provide video coding and decoding (codec) functions, and a network time protocol program codes 512 for directing the processor to provide network time protocol (NTP) functions.

The variable memory 514 includes a plurality of storage locations including an input signal transmit buffer 516 for storing timestamped input signals. The variable memory 106 may be implemented in random access memory or flash memory, for example. The surgeon-side processing circuitry 500 also includes a real-time clock 542, which may be queried by the processor 502 to provide the current time.

The I/O 522 includes an input interface 530 for receiving surgeon input signals from the surgeon input console 114. The input interface 530 may be implemented as a Controller Area Network (CAN bus) interface.

The I/O 522 also includes a network interface 532 connected to transmit and receive data over the network 208. In this configuration, the network interface 532 receives an in-patient image video stream from the network 208. The I/O 522 further includes a display interface 534 for producing display signals for driving the display 120 of the surgeon input console 114. The processor 502 can be configured to decode the in-patient image video stream using functions implemented by executing the video codec program codes 510. In some instances, the processing circuitry 500 may include an optional hardware video codec 536, which offloads the video decoding from the processor 502 and preforms hardware-based decoding of the in-patient image video image stream. The network interface 532 also transmits the timestamped input signals to the patient-side-interface 206 via the network 208 and receives and/or transmits data logs and information to the data store 304.

The surgeon-side interface 204 may be partly or fully implemented using a hardware logic circuitry including discrete logic circuits, an application specific integrated circuit (ASIC), and/or a field-programmable gate array (FPGA). The surgeon-side processing circuitry 500 may include a graphics processing unit (GPU) for accelerating some operations such as the execution of the video codec program codes 510.

The surgeon-side interface 204 may be implemented as one or more hardware circuitry modules included in the surgeon input console 114. The surgeon-side interface 204 may be implemented as software and/or firmware instructions executable on one or more processors, controllers, ASICs, FPGAs, or dedicated hardware. For instance, the instructions can be executed by the processing circuitry of the surgeon input console 114. In some cases, the surgeon-side interface 204 can be implemented partly as software and/or firmware instructions and partly as one or more hardware circuitry modules that are separate from or part of the surgeon input console 114. The surgeon-side interface 204 can be integrated with the surgeon input console 114, which can encompass being wholly separate from the surgeon input console 114 or being wholly or partially a portion of the surgeon input console 114.

Patient-Side Interface

Figure 5B:
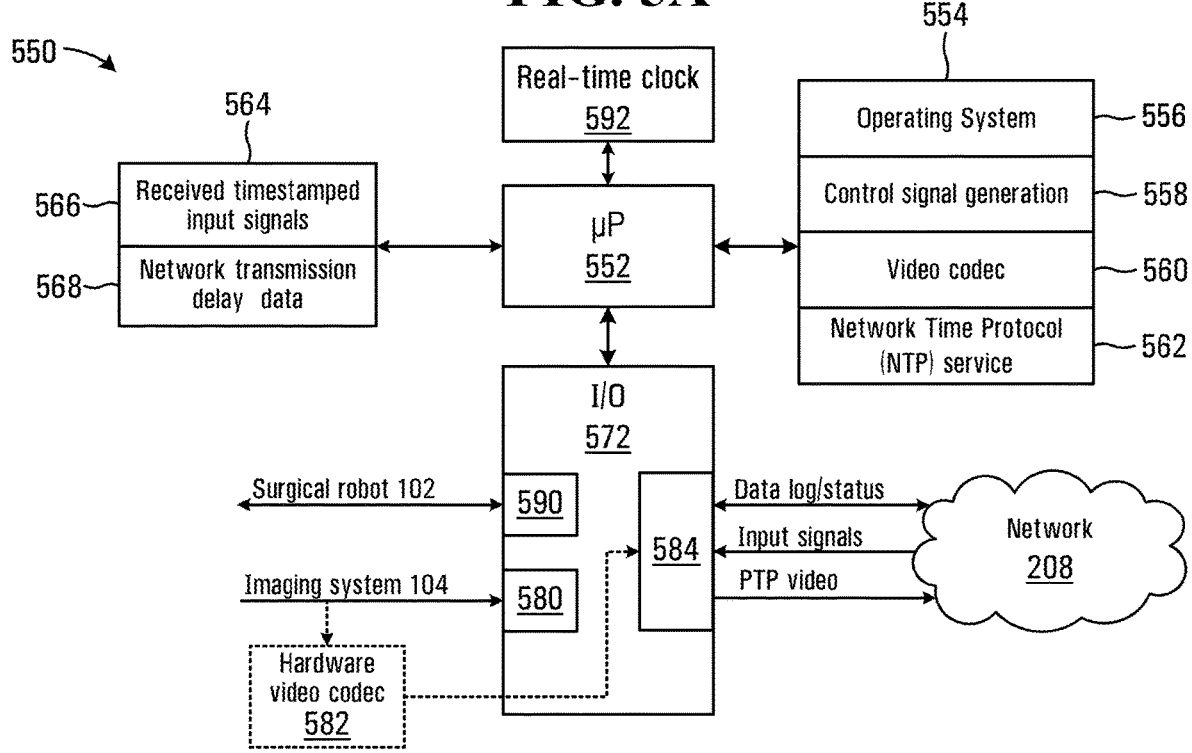
FIG. 5B is a block diagram of a processing circuitry for implementing the patient-side interface.

The patient-side interface 206 may similarly be implemented using the processing circuitry shown generally at 550 in FIG. 5B. Referring to FIG. 5B, the patient-side processing circuitry 550 includes a processor 552, a program memory 554, a variable memory 564, and an input output port (I/O) 572, all of which are in communication with the processor 552.

Program codes for directing the processor 552 to carry out various functions are stored in the program memory 554, which may be implemented as a random-access memory (RAM) and/or a hard disk drive (HDD), or a combination thereof. The program memory includes operating system program codes 556 for directing the processor 552 to provide operating system functions, a control signal generation program codes 558 for directing the processor to generate control signals for the robotic surgery system 100, video codec program codes 560 for directing the processor to provide video coding and decoding (codec) functions, and network time protocol program codes 562 for directing the processor to provide network time protocol (NTP) functions.

The variable memory 564 includes a plurality of storage locations including a timestamped input signal storage location 566 for storing timestamped input signals received from the surgeon-side interface 204, and a transmission delay data storage location 568 for storing network transmission delay data. The variable memory 564 may be implemented in random access memory or flash memory, for example. The patient-side processing circuitry 550 also includes a real-time clock 592, which may be queried by the processor 552 to provide the current time.

The I/O 572 includes an interface 580 for receiving an image video stream from the in-patient imaging system 306. The processor 552 can be configured to encode the in-patient image video stream for transmission over the network using functions implemented by executing the video codec codes stored in the second block of program codes 558. The encoded video stream has a higher compression level than raw video data and is more efficiently transmitted over the network 208. The processing circuitry 550 may include an optional hardware video codec 582, which offloads the video encoding from the processor 552 and preforms hardware encoding of the in-patient image video image stream. The I/O 572 further includes a network interface 584 connected to transmit and receive data over the network 208. The network interface 584 is used to transmit the encoded video signals over the network 208 to the surgeon-side interface 204.

The network interface 584 is also used to receive timestamped input signals from the surgeon-side interface 204 via the network 208 and to receive and/or transmit data logs and information to the data store 304.

The I/O 572 further includes an output interface 590 for delivering control signals to the robotic surgery system 100. The output interface 590 may be implemented as a Controller Area Network (CAN bus) interface.

The patient-side interface 206 may be partly or fully implemented using a hardware logic circuitry including discrete logic circuits, an application specific integrated circuit (ASIC), and/or a field-programmable gate array (FPGA). The patient-side processing circuitry 550 may include a graphics processing unit (GPU) for accelerating some operations such as the execution of the video codec program codes 560.

The patient-side interface 206 may be implemented as one or more hardware circuitry modules included in the robotic surgery system 100. The patient-side interface 206 may be implemented as software and/or firmware instructions executable on one or more processors, controllers, ASICs, FPGAs, or dedicated hardware. For instance, the instructions can be executed by the processing circuitry of the robotic surgery system 100. In some cases, the patient-side interface 206 can be implemented partly as software and/or firmware instructions and partly as one or more hardware circuitry modules that are separate from or part of the robotic surgery system 100. The patient-side interface 206 can be integrated with the robotic surgery system 100, which can encompass being wholly separate from the robotic surgery system 100 or being wholly or partially a portion of the robotic surgery system 100.

Any of the video codes or image codecs can utilize artificial intelligence (AI), which can reduce latency and improve quality of coding and decoding. For example, an AI-enabled video or image codec can reduce the size of encoded video or images, which can improve latency or other characteristics of transmission over one or more networks.

Method for Remotely Controlling Robotic Surgery

Figure 6:
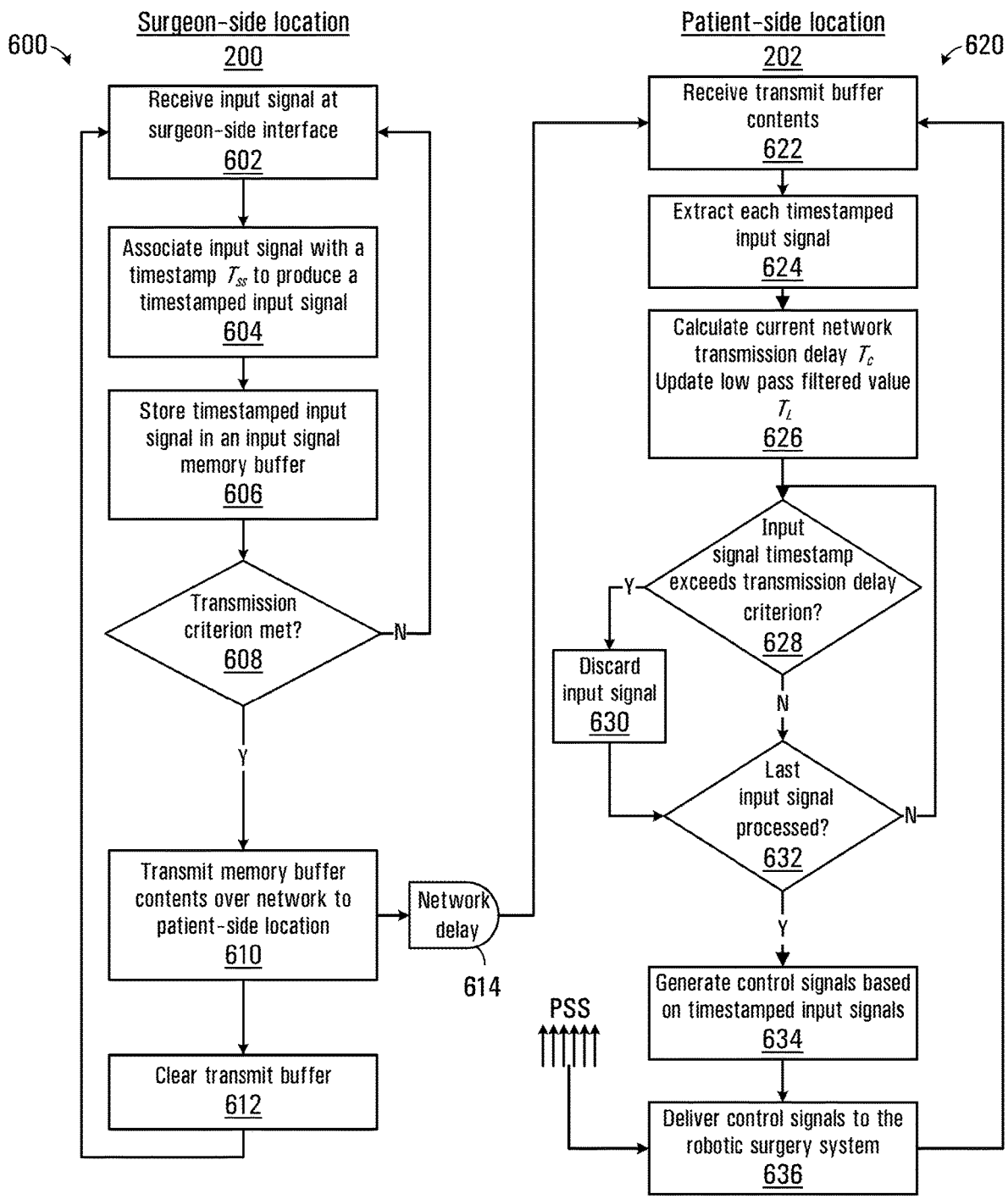
FIG. 6 is a process flowchart depicting blocks of code for directing the surgeon-side processing circuitry to generate and transmit timestamped input signals to the patient-side processing circuitry.

Referring to FIG. 6, a process flowchart depicting blocks of code for directing the surgeon-side processing circuitry 500 to generate and transmit timestamped input signals is shown generally at 600. The blocks generally represent codes that may be read from the program memory 504 for directing the surgeon-side processing circuitry 500 to process the input signals from the surgeon input console 114. The actual code to implement each block may be written in any suitable program language, such as C, C++,C #, Java, and/or assembly code, for example.

The process 600 starts at block 602, which directs the processor 502 to receive an input signal from the surgeon input console 114 at the input interface 530. In this configuration, the SSS signal acts as a sampling signal that causes the current position of each of the handles 116 to be encoded into motion input signals by the respective input devices and transmitted over a communications bus to the surgeon-side processing circuitry 500. Additionally, the state of other input signals from pedals or control features on the handles 116 are similarly sampled and transmitted to the surgeon-side processing circuitry 500.

Figure 7:
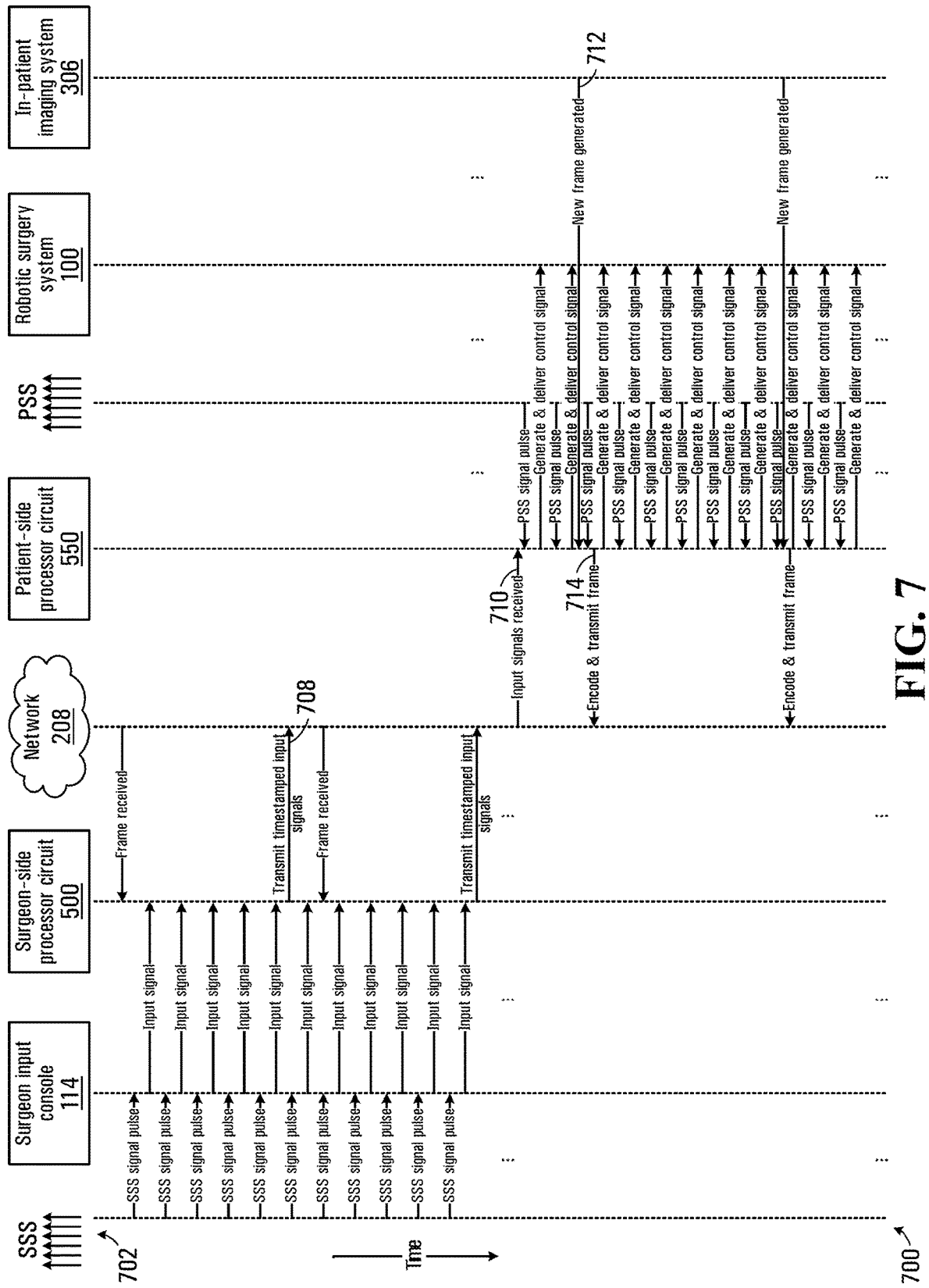
FIG. 7 is a graphical depiction of signal transmissions between the surgeon-side location and patient-side location.

Referring to FIG. 7, the signal transmissions between various components at the surgeon-side location 200 and patient-side location 202 are illustrated graphically as a function of time at 700. Referring to FIG. 7, the SSS signal 702 causes sequential SSS signal pulses to be received at the surgeon input console 114. In this example the SSS signal pulses are spaced apart at substantially fixed time intervals, but as noted above the signal pulses need not necessarily be regularly periodic and may have some asynchronicity. The input devices at the surgeon input console 114 respond by generating and transmitting successive input signals to the surgeon-side processing circuitry 500. For sake of illustration in the example shown in FIG. 7, input signals are illustrated for only one input device although in practice input signals would be received from both input devices and other controls of the surgeon input console 114.

Referring back to FIG. 6, block 604 then directs the processor 502 to associate each input signal with a timestamp $T_{ss}$ indicating a time at which the input signal was received at the surgeon-side processing circuitry 500. In some implementations, the left-hand and right-hand input devices, pedals, and other controls of the surgeon input console 114 may communicate input signals over a shared bus. In this case, input signals sampled by the left and right input devices in synchronism with the SSS signal may be received at the surgeon-side processing circuitry 500 at slightly different times. The timestamp $T_s$ may represent the time of receipt of the signal rather than the exact time of generation of the input signal at the input device of the surgeon input console 114.

Each input signal may be represented in a data message having several bytes of data encoding the state and position of the respective handle 116, pedal, or control. The timestamp may thus be appended to the data message to generate the timestamped input signal. In this example, the timestamp is generated by querying the real-time clock 542 to determine the current time of day. Synchronization of the real-time clock 542 is maintained by executing the network time protocol program codes 512 in the program memory 504 to provide network time protocol services that periodically updates the real-time clock against a reference NTP clock. In some instances, the program codes 512 may initiate execution of a chrony implementation of a network time protocol client service, which facilities time synchronization in the millisecond range or better.

Block 606 then directs the processor 502 to write the timestamped input signal data message to the transmit buffer 516 in the variable memory 514. In the configuration shown in FIG. 6 and FIG. 7, several timestamped input signals are accumulated in the transmit buffer 516 of variable memory 514. Block 608 then directs the processor 502 to determine whether a transmission criterion has been met. If the transmission criterion has not yet been met, the processor 502 is directed back to block 602 and blocks 602 to 606 are repeated for the next input signal received from the surgeon input console 114. If at block 608, the transmission criterion has been met, the processor 552 is directed to block 610.

Any of a plurality of transmission criteria may be implemented at block 608. In Each input signal may be transmitted immediately after being timestamped. In some cases, the transmission criterion may be based on a fixed number of timestamped input signals being accumulated in the buffer. In some instances, the number of timestamped input signals to be accumulated in the buffer may be calculated based on network conditions or other considerations.

The transmission criterion may be linked to the receipt of video image frames, thus imposing a link between input signals transmission and receipt of video images. For example, the transmission criterion may be considered to be met when a new image frame generated by the in-patient imaging system 306 at the patient-side location 202 has been received at the network interface 532 of the surgeon-side processing circuitry 500.

Referring back to FIG. 6, the process 600 continues at block 610, which directs the processor 502 to cause the network interface 532 to transmit the data contents of the transmit buffer 516 over the network 208 to the processor 552 at the patient-side location 202. Data may be transmitted over the network 208 using a real-time communication protocol. For example, Web Real-Time Communication (RTP) is an open-source implementation of a protocol that provide for direct peer-to-peer communication of video, audio and other data over a network. Real-Time Transport Control Protocol (RTCP) works with RTP to monitor Quality of Service parameters for data delivery over the network. Other real time communication protocols may be implemented in place of RTP/RTCP.

Referring again to FIG. 7, the effect of this transmission criterion is illustrated. A previously received image frame is shown at 704 and the next received new image frame is shown at 706. In the interim between the receipt of frames 704 and 706, in the example shown five separate input signals have been received, timestamped, and added to the transmit buffer 516. At 708, the timestamped input signals in the transmit buffer 516 are transmitted together at the same time over the network 208. The transmission of several signals at a time may have the advantage of reducing transmission overhead. As noted above, more or less than five input signals may be transmitted at the same time or each input signal may be individually transmitted.

Block 610 then directs the processor 502 to block 612. Block 612 directs the processor 502 to clear the contents from the transmit buffer 516, since these control signals would have now been transmitted. Block 612 then directs the processor 502 back to block 602 to repeat the process 600.

The transmission of the contents of the transmit buffer 516 to the patient-side processing circuitry 550 will undergo a network delay 614, which as disclosed above may vary based on the distance of transmission, the quality of the network, and various other factors that affect transmission time.

Still referring to FIG. 6, a process flowchart depicting blocks of code for directing the patient-side processing circuitry 550 to generate control signals in accordance with an example shown generally at 620. Block 622 directs the processor 552 to receive the contents of the transmit buffer at the network interface 584. If the transmit buffer includes more than one input signal, block 624 directs the processor 552 to process the transmit buffer contents to extract each individual timestamped input signal. Block 624 also directs the processor 552 to write the timestamped input signals to the location 566 of the variable memory 564.

Block 626 then directs the processor 552 to query the real-time clock 592 (which can be synchronized with the real-time clock 542) and to calculate the current network delay $T_c$. In this implementation, ongoing processing of the transmission delay values $T_c$ is then used to generate a low pass filtered transmission delay value $T_L$. Block 626 directs the processor 552 to update the value of $T_L$, which is stored in the storage location 568.

Block 628 then directs the processor 552 to query the real-time clock 592 and determine, for each timestamped input signal written to the storage location 566, whether the timestamp exceeds a transmission delay criterion. The transmission delay criterion may be implemented as a maximum transmission delay (such as, about 200 msec). Network jitter may also be used in addition or in the alternative as the transmission delay criterion since even small amount of network jitter may negatively affect performance, as described herein.

If the timestamp exceeds the transmission delay criterion, block 628 directs the processor 552 to block 630, which directs the processor discard or delete the input signal from the storage location 566. Block 630 then directs the processor 552 to block 632. If at block 628, the current timestamped input message is found to be within transmission delay criterion time the processor 552 is directed to block 632.

Block 632 then directs the processor 552 to determine whether the last timestamped input signal in the storage location 566 has been processed, in which case the processor is directed to block 634. If there remain timestamped input signals in the storage location 566 to be processed, block 632 directs the processor 552 back to block 628.

Block 634 then directs the processor 552 to read the remaining (or non-discarded) timestamped input signals in the storage location 566 and to generate control signals based on the timestamped input signals. The control signals are generated in a format suitable for causing actuation of movement or other operations of the surgical instruments 102-108 by the robotic surgery system 100. Block 636 then directs the processor 552 to deliver the control signals to the robotic surgery system 100.

In some cases, a control signal is generated at block 634 for each timestamped input signal remaining in the timestamped input signal storage location 566. At block 636, the delivery of each individual control signal is synchronized to successive pulses of the PSS signal. Referring again to FIG. 7, the receipt of the input signals is shown at 710 and the patient-side processing circuitry 550 generates the corresponding control signals. In this example where five input signals are received, the PSS signal pulses are used to synchronize delivery of the five corresponding generated control signals. Since the PSS signal has the same frequency as the SSS signal at the surgeon-side location 200, the control signals are thus delivered to the robotic surgery system 100 with a similar time-spacing between successive control signals. Each control signal effectively includes the same movement data as the corresponding input signal. However, since some of the input signals may have been discarded at block 630, the control signals may not have a one-to-one correspondence with the input signals.

Still referring to FIG. 7, when a new frame is generated by the in-patient imaging system 306 (such as shown at 712), the patient-side processing circuitry 550 encodes and transmits the frame with some delay at 714. New frames continue to be generated, encoded and transmitted to the surgeon-side location 200 at intervals that depend on the frame rate of the in-patient imaging system 306. The transmitted frames are received at the surgeon-side processing circuitry 500 after transmission over the network 208.

In some cases, the block 634 may further direct the processor 502 to interpolate between successive input signals such that the generated control signal is based on more than one timestamped input signal. The interpolation can be used to generate input signals when one or more of a series of signals have not been successfully delivered to the patient-side location 202 or, in some cases, when one or more signals have been discarded. Interpolation can be performed to determine a missing input signal between a pair of received input signals. If one of the signals in the pair has been received, interpolation may not be possible. In this case, prior input signals may be used to predict the missing input signals by implementing a predictive function, such as Kalman filtering.

In some implementations, the robotic surgery system 100 may be expecting the input signals to be provided at a certain threshold rate (such as, the rate of the PSS signal). When the input signals received by the patient-side processing circuitry 550 do not satisfy such threshold rate, the processor 552 can repeat at least some of the received input signals or otherwise modify the input signals in order to provide the input signals to the robotic surgery system 100 at the threshold rate. The threshold rate may not be satisfied as a result of input signals not being received by the patient-side processing circuitry 550 at a sufficient rate (because of, for instance, network delay) or due to one or more input signals having been discarded, among others.

In some instances, interpolation or prediction can be used for data received from the patient-side interface 206.

The configurations disclosed above provide methods and systems for maintaining synchronization between the surgeon inputs at the input console 114 and the operations performed by the robotic surgery system 100 in absence of a wired connection that would enforce synchronization. The timestamping of the input signals at the surgeon-side location 200 facilitates generation of control signals at the patient-side location 202 that will prevent unintended motions of the actuable surgical instruments 102-108. The process implementations also correct for network issues, such as for example some input signals arriving out of order at the patient-side location 202.

Network Redundancy

Figure 8:
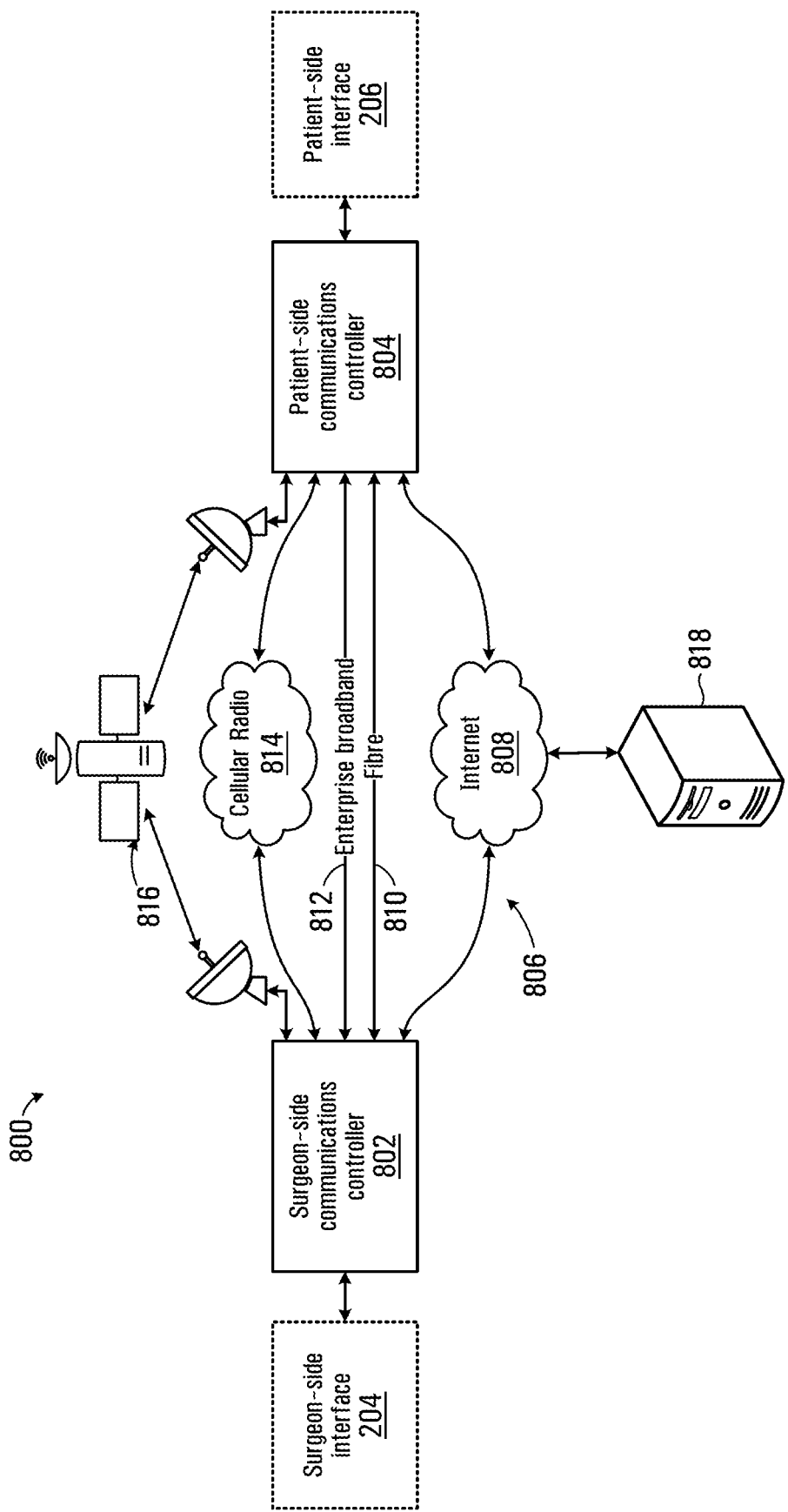
FIG. 8 is a block diagram of a network implementation.

Referring to FIG. 8, an example for implementing the network 208 is shown generally at 800. The network 800 includes a surgeon-side communications controller 802 in communication with the surgeon-side interface 204. The network 800 also includes a patient-side communications controller 804 in communication with the patient-side interface 206. The surgeon-side communications controller 802 is in communication with a plurality of available networks 806 connecting between the surgeon-side location 200 and the patient-side location, where the patient-side communications controller 804 is in communication with the plurality of available networks.

The plurality of available networks 806 may also include a connection to the internet 808, which may be provided by an internet service provider or other provider that guarantees specific performance metrics via a service level agreement (SLA). For example, some service providers may guarantee traffic prioritization through their routers and switches, reduced latency, and or guaranteed bandwidth. The plurality of available networks 806 may also include a fiber optic network 810, which may be shared or dedicated, or an enterprise broadband network 812 such as may be provided via dedicated lines leased from a telecommunications company. The plurality of available networks 806 also include a connection via a radio network 814 such as a GSM or other cellular radio network. The plurality of available networks 806 may also include a satellite network 816. Various other shared or dedicated networks may be included in the plurality of available networks 806 depending on availability.

In the configuration shown, the surgeon-side communications controller 802 and patient-side communications controller 804 each connect to a performance management server 818. In this configuration, the performance management server 818 connection is via the internet 808, but in other configurations the connection may be via any of the other plurality of available networks 806 or the performance management function may be provided at either the surgeon-side location 200 or the patient-side location 202. Generally, the networks 806 will differ in their data throughput capacity, potential transmission delay, and reliability. The performance management server 818 monitors various performance metrics associated with the plurality of networks in real-time and makes performance information associated with the performance metrics available to the patient-side communications controller 804 and the surgeon-side communications controller 802.

The network 800 may be configured as a software-defined wide area network (SD-WAN) architecture in which the communications controllers 802 and 804 may be implemented as SD-WAN devices, such as edge devices. The SD-WAN devices may not necessarily be physical devices and may be incorporated in the surgeon-side interface 204 or the patient-side interface 206. The performance management server 818 may implement an SD-WAN controller and/or SD-WAN orchestrator functions. In a SD-WAN architecture, the orchestrator and controller functions can dynamically manage the flow of data over the available networks and determine the priority level for various data flows. SD-WAN architecture can allow for an automatic selection of one or more selected networks from the plurality of available networks 806 based on performance information. In addition, the selection of such one or more networks can be continuously updated based on performance information. For example, assuming that first and second networks had been selected for transmission of data and it is subsequently determined that performance of another network exceeds performance of the first network, the first network can be replaced with another network. As a result, transmission of data subsequent to the determination that performance of another network exceeds performance of the first network would continue over the second network and another network. For instance, as explained herein, critical signals can be implemented as an "on" signal followed by an "off" signal, and the "on" signal may be transmitted over the first and second networks while the "off" signal may be transmitted over the second network and another network.

The network 800 shown in FIG. 8 facilitates communication between the surgeon-side interface 204 and patient-side interface 206 generally as described above in connection with the network 208 shown in FIG. 2. However, in this configuration, the data flows between the surgeon-side interface 204 and patient-side interface 206 are dynamically configured by the communications controllers 802 and 804 to meet the requirements for remote control of the robotic surgery system 100.

Figure 9:
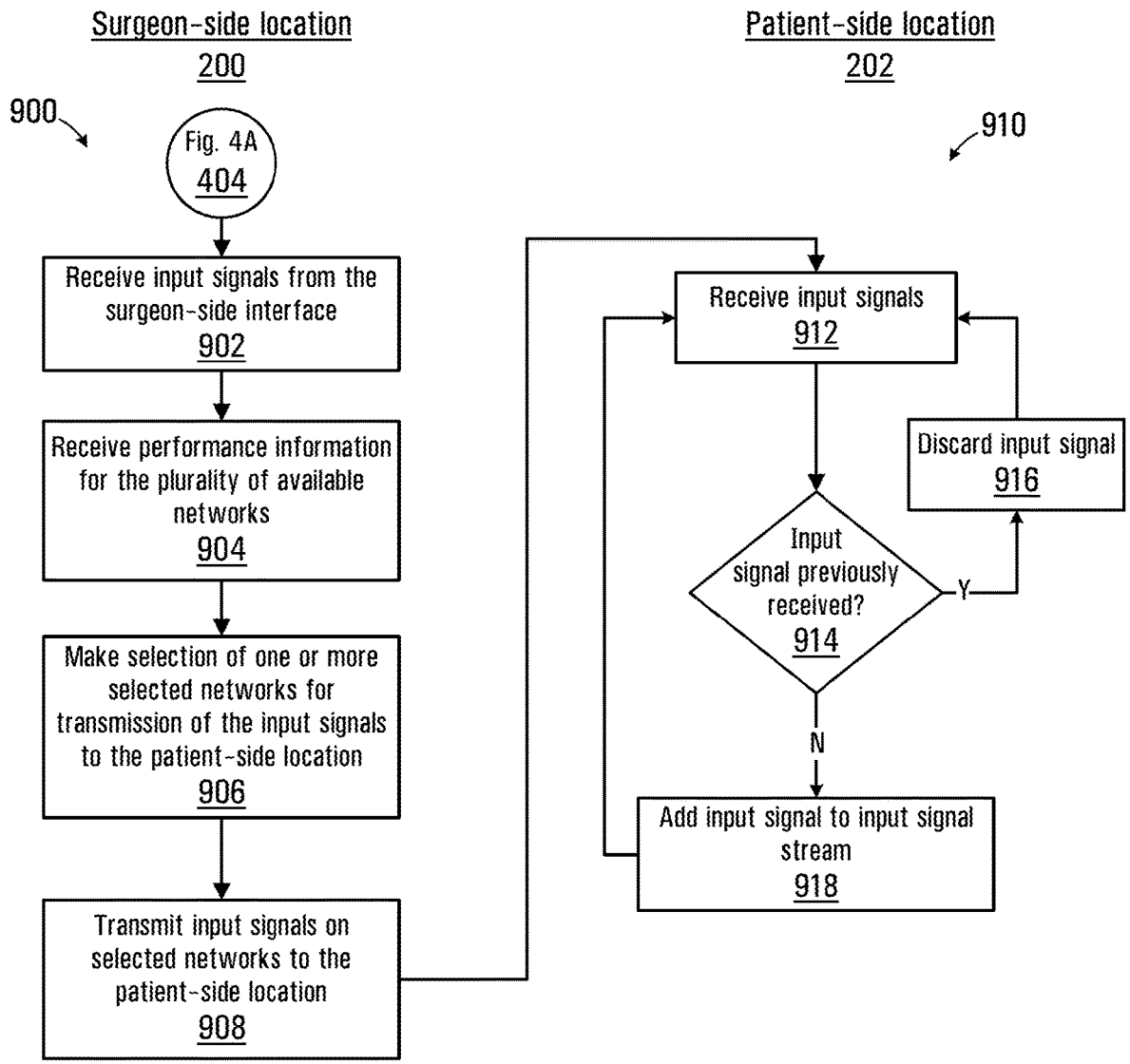
FIG. 9 is a flowchart depicting functions performed for a surgeon-side to patient-side transmission using the network implementation shown in FIG. 8.

Referring to FIG. 9, a flowchart depicting functions performed by the surgeon-side communications controller 802 for transmitting input signals to the patient-side location 202 is shown generally at 900. The timestamped input signals are generated by the surgeon-side interface 204 in accordance with block 404 of the process 400 and are received at block 902. While the process 900 is described with reference to timestamped input signals, in some instances, the input signals may not be timestamped and/or may be in a stream format other than described above.

As shown at block 904, performance information is received from the performance management server 818 for the plurality of available networks 806. The performance information may include transmission metrics such as packet loss, real-time transmission delay, bandwidth, and network jitter. While maintaining a low transmission delay is important for remote control of the robotic surgery system 100, time variance in transmission delay is also an important metric to consider. Time variance in transmission delay is generally referred to as network jitter. Since the input signals and in-patient image video stream are sequential in nature, network jitter causes a disruption in the normal sequence of sending input signals and video data over the network 800. This may result in unpredictability in commanded movements at the robotic surgery system 100 or poor video quality at the surgeon-side location 200.

As shown at block 906, the surgeon-side communications controller 802 is further functionally configured to make a selection of one or more selected networks from the plurality of available networks 806 based on the performance information. In some implementations, a selection of a primary network (or primary networks) and a secondary network (or secondary networks) may be made by the surgeon-side communications controller 802 based on the performance information. As an example, the fiber optic network 810 may be selected as the primary network, with the enterprise broadband network 812 being selected as a secondary network. The selection of the primary network(s) and secondary network(s) may be repeated either periodically or when there is a change in the performance information associated with the plurality of available networks 806. In some cases, where there are several high-performance networks within the plurality of available networks 806, the surgeon-side communications controller 802 may select more than just one primary and secondary network for conducting transmissions.

In some cases, the patient-side communications controller 804 can make a selection of one or more selected networks from the plurality of available networks 806 based on the performance information. For example, the patient-side communication controller 804 can make the selection in order to effectively transmit the image video stream, as described herein.

Having selected the primary and secondary networks, several options become available for transmission of data between the surgeon-side location 200 and the patient-side location 202. Input signals may be targeted for transmission over the primary network(s) until a problem or failure is encountered with the transmission of the input signals. At this time the patient-side communications controller 804 may be configured to revert to transmission over the secondary network(s) until the problem resolves. In some cases, each input signal may be transmitted on both the primary network(s) and the secondary network(s). In some implementations, a selected primary network(s) would generally provide for the lowest transmission delay and/or lowest network jitter. However, in the event of an abnormal transmission delay and/or network jitter on the primary network(s), the copy of the input signal transmitted on the secondary network(s) may arrive at the patient-side location 202 before the same input signal transmitted on the primary network(s). In this case, the secondary network(s) provides a redundant transmission that may be used in the event of such a failure.

In a further instance, input signals may be targeted for transmission over the primary network(s) and the secondary network(s) may be used to transmit other data, such as event-oriented notifications. In some cases where the primary network(s) and the secondary network(s) have similar performance, the input signals may be divided for transmission such that some of the input signals are transmitted on the primary network(s) and other input signals are transmitted on the secondary network(s). For example, the patient-side communications controller 804 may alternate between using the primary network(s) and the secondary network(s) for successive input signal transmissions.

As disclosed above, there may be several different types of input signals and image data that are transmitted over the network. The input signals include the motion input signals representing the position of the handles 116 of the surgeon input console 114, actuation signals that actuate operations at the surgical instruments 102-108, clutch signals for temporarily decoupling the surgical instruments 102-108, the electrocautery signals for turning on or turning off an electrocauterization current to an instrument to cauterize tissue, haptic feedback signals, and force feedback signals. There will typically be many more motion input signals than the other input signals transmitted to the patient-side location 202. If some of the motion input signals (or image data) are not successfully transmitted or transmitted with a delay, the operations of the robotic surgery system 100 may not be significantly impacted. For example, even if a whole packet of five input signals were missing, this would only represent a very short period of time (for instance, extending over 25 milliseconds assuming 200 Hz sample rate). Interpolation or prediction may be used to fill in for the missing input signals, or at worst the commanded motion may have a slight discontinuity.

However, some of the above input signals may be considered as critical input signals that have the potential to cause harm to the patient 110 (due to, for example, cutting tissue) if delayed or not delivered to the patient-side location 202. For example, an electrocautery signal may be implemented as an "on" signal that switches on the electrocautery current for one of the instruments 102-108 followed by an "off" signal that switches off the electrocautery current. If the "off" signal were to not reach the patient-side location 202 or be delayed, this would result in electrocautery instrument continuing delivery of the current for longer than desired by the surgeon 112. Since the electrocautery current is activated to burn tissue, the unintended elongation of the time for which the current is active can result in tissue damage. In another example, the clutch signal, which is usually activated by depressing a foot pedal, causes the servo motors of the robotic surgery system 100 to be temporarily idled until the foot pedal is released. As in the previous example, this may involve transmission of an "on" clutch signal followed by an "off" clutch signal. If either the "on" or "off" clutch signal were to be delayed or go missing, unintended movements or lack of movement of the instruments 102-108 may result at the patient-side location 202. This could have potential to cause injury or tissue damage to the patient 110 since the instruments 102-108 may move unpredictably or unintendedly within the surgical site. Other potentially harmful situations could occur when switching between instruments in multi-instrument robotic surgery systems. If an input signal related to an instrument change is lost or delayed in transmission, the resulting confusion could lead to patient injury or tissue damage. The clutch signals, electrocautery signals, and instrument change signals may be considered as critical input signals that should be targeted for a lossless transmission to the patient-side location 202.

More generally, critical input signals can include signals (such as, "on" and/or "off" signals) for controlling needle drivers, scissors, staplers, clip appliers, removers, dissection instruments, cutting instruments, or coagulation instruments. Critical input signals can include signals for controlling instruments that deliver energy, as described herein.

In some instances, critical input signals may not include distinct "on" and "off" signals, but rather may include a single signal. Presence of such single signal can correspond to the "on" signal, and absence of such single signal can correspond to the "off" signal (or vice versa). For example, presence of a signal can indicate a command to activate the electrocautery current for one of the instruments 102-108, while subsequent absence of the signal can indicate a command to deactivate the electrocautery current.

In some implementations, when the "off" signal is not received within a duration of time, the patient-side interface 206 can be configured to generate the "off" signal and provide such signal to the robotic surgery system 100 in order to not harm the patient 110. This can prevent injury or tissue damage to the patient 110 in case if a malfunction, such as loss of the network connection. For example, the "off" signal (or similar indication) for electrocautery can be generated in case it has not been received within 100 msec (or less or more) of the receipt of the "on" signal for electrocautery.

Critical input signals that have potential for causing harm if not timely delivered may be targeted for transmission over the most reliable of the available networks, which would be the primary network(s) in this case. Additionally, such input signals may also be targeted for transmission over at least two of the available networks. In some instances, if at block 904 a minimum quality of service is not met for at least one of the primary and secondary networks, the operation of the robotic surgery system 100 may be inhibited to prevent undue risk. For example, if the surgeon-side communications controller 802 or patient-side communications controller 804 are unable to select at least one or at least two networks from the plurality of available networks 806 that meet a minimum performance criterion (or criteria), the respective surgeon-side interface 204 or patient-side interface 206 may be configured to inhibit further operation of the robotic surgery system 100. This can include inhibiting transmission of critical input signals, while possibly allowing transmission of other, non-critical input signals.

At block 908, the input signals are then transmitted to the patient-side location 202 in accordance with the networks selected at block 906. As described above, several time-stamped input signals may be combined for more efficient transmission over the network in a single data packet. In such cases the transmission may include transmission of data packets each including several input signals.

Figure 10:
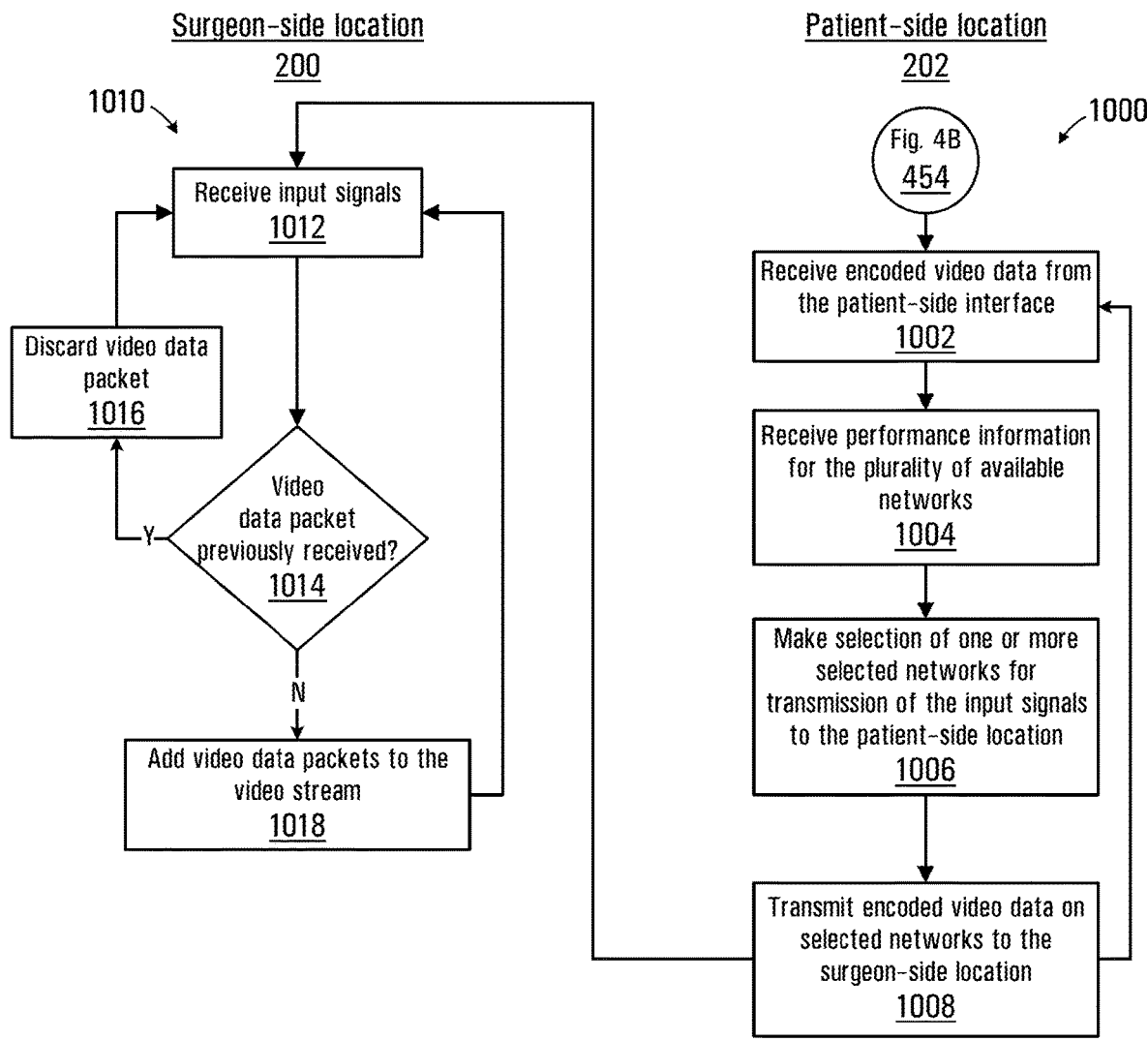
FIG. 10 is a flowchart depicting functions performed for a patient-side to surgeon-side transmission using the network implementation shown in FIG. 8.

A flowchart depicting functions performed by the patient-side communications controller 804 for receiving the input signals is shown generally at 910 in FIG. 9. Input signals are received over the network 800 at block 912. At block 914, a determination is made as to whether each received input signal or packet of input signals has been previously received at the patient-side location 202. In the above example where input signals are redundantly transmitted on both the primary and secondary network(s), the input signals or data packet(s) including several input signals may have already been received at the patient-side communications controller 804. In some cases, if the currently received input signal is a copy of an input signal already received, the input signal is discarded at block 916. At block 914 when the input signal has not been previously received, the process 910 continues at block 918 where the input signal is added to the input signal stream for processing by the patient-side interface 206 generally as described above. Blocks 912-918 of the process 910 and blocks 902-908 of the process 900 are continually repeated during operation of the robotic surgery system 100. Referring to FIG. 10, a flowchart depicting functions performed by the patient-side communications controller 804 for transmitting encoded video data representing image frames captured by the in-patient imaging system 306 is shown generally at 1000. The encoded image frames are generated at block 454 of the process 450 executed on the patient-side interface 206 and are received at block 1002 of the process 1000. At block 1004, performance information is received from the performance management server 818 for the plurality of available networks 806. At block 1006, the patient-side communications controller 804 is functionally configured to make a selection of one or more selected networks from the plurality of available networks 806 based on the performance information. The selection process is generally as described above in connection with the process 900 shown in FIG. 9. As in the case of the transmission of input signals from the surgeon-side location 200 to the patient-side location 202, a selection of primary network(s) and secondary network(s) may be made by the patient-side communications controller 804 based on the performance information. The encoded video data may thus be transmitted via the primary and/or secondary networks, generally as described above.

At block 1008, the encoded video data is transmitted over the selected networks to the surgeon-side location 200.

A flowchart depicting functions performed by the surgeon-side communications controller 802 for receiving the video data is shown generally at 1010. The encoded video data is received over the network 800 at block 1012. At block 1014, a determination is made as to whether each received video data packet has been previously received at the surgeon-side location 200. In implementations where video data is redundantly transmitted on both the primary and secondary networks, the video data packets may have already been received at the surgeon-side communications controller 802. In some cases, if the currently received video data packet is a copy of a video data packet already received, the packet is discarded at block 1016. At block 914 when the video data packet has not been previously received, the process 1010 continues at block 1018 where the video data packets are added to the video stream prior to being decoded into image frames by the surgeon-side interface 204. Blocks 1012-1018 of the process 1010 and blocks 1002-1008 of the process 1000 are continually repeated during operation of the robotic surgery system 100.

The network 800 has the advantage of including the plurality of available networks 806 for selection by the communications controllers 802 and 804 for transmission of data. The availability of more than one network facilitates selection of alternative transmission networks and well of redundancy by transmitting two or more copies of the same data over different selected networks. The dynamic real-time performance monitoring also facilitates configuration of a network that is responsive to changing performance conditions. In some cases, selection of one or more networks of the plurality of available networks 806 can be made in view of costs associated with the transmission of data. For instance, transmission over one or more of the available networks can be charged on per-byte (or another data unit) basis, and such one or more networks may not be selected when one or more cheaper alternative networks are available. One or more networks higher cost networks can include cellular or satellite networks.

In some instances, the communications controllers 802 and 804 may select all networks of the plurality of available networks 806 for transmission of data.

In some implementations, Web Real-Time Communication (WebRTC) can be used for communicating data between the surgeon-side interface 204 and the patient-side interface 206. Advantageously, WebRTC can be operated in a mode that guarantees delivery of data (and will automatically retry and retransmit data in case of losses).

Example Implementations

A method for remotely controlling a robotic surgery system located at a patient-side location can include: receiving a plurality of input signals from a surgeon input console disposed at a surgeon-side location that is remote from the patient-side location; associating each input signal with a timestamp to generate a timestamped input signal, the timestamp indicating a time at which the input signal was received; transmitting the timestamped input signals over a network to the patient-side location; receiving the timestamped input signals at the patient-side location and generating a plurality of control signals for controlling operations of the robotic surgery system, each control signal being based on one or more timestamped input signals; and delivering the control signals to the robotic surgery system at times based on the timestamp of the respective one or more timestamped input signals.

The method of any of the preceding paragraphs and/or any of the methods disclosed herein can have one or more of the following features. Receiving the plurality of input signals can include receiving input signals representing positions of one or more hand controllers of the surgeon input console at successive times corresponding to a surgeon-side input sampling rate. Associating each input signal with a timestamp can include receiving each input signal at a surgeon-side interface and associating the input signal with a timestamp corresponding to a time at which the input signal is received at a surgeon-side interface in communication with the surgeon input console. Each input signal can include data representing the position of the one or more hand controllers and wherein associating each input signal with a timestamp can include embedding timestamp data in the input signal to generate the timestamped input signal. Transmitting the timestamped input signals can include accumulating a plurality of timestamped control signals in an input signal memory buffe and transmitting the plurality of timestamped control signals accumulated in the input signal memory buffer over the network to the patient-side location when a transmission criterion is met. The method can include receiving a plurality of image frames at the surgeon-side location from an in-patient imaging system located at the patient-side location, wherein the transmission criterion is based on a new image frame being received from the in-patient imaging system.

The method of any of the preceding paragraphs and/or any of the methods disclosed herein can have one or more of the following features. Receiving the plurality of input signals can include receiving input signals representing positions of one or more hand controllers of the surgeon input console at successive times corresponding to a surgeon-side input sampling rate and wherein receiving the plurality of image frames can include receiving image frames at a frame rate that is less than the input sampling rate. Transmitting the timestamped input signals can include transmitting the timestamped input signals over the network using a real-time communication protocol. The method can include generating the timestamp based on a time provided by a surgeon-side real-time clock and synchronizing the surgeon-side real-time clock with a network based real-time clock using a network time protocol. Transmitting the timestamped input signals can include transmitting encrypted timestamped input signals. Receiving the plurality of input signals can include receiving input signals from an input device associated with the surgeon input console prior to any processing of the input signals that would increase a bandwidth required for transmission of the input signals.

The method of any of the preceding paragraphs and/or any of the methods disclosed herein can have one or more of the following features. Delivering the control signals to the robotic surgery system at times based on the timestamp of the respective one or more timestamped input signals can include delivering the control signals at time intervals that substantially correspond to time intervals between the respective timestamps of the timestamped input signals. Generating the plurality of control signals can include generating an ordered plurality of control signals based on the timestamp in the corresponding timestamped input signal. The method can include discarding input signals that have a timestamp that meet a transmission delay criterion prior to generating the plurality of control signals. The method can include calculating a current network transmission delay time based on a time of receiving one or more of the timestamped input signals at the patient-side location. The method can include processing successively calculated current network transmission delay times to generate a smoothed network transmission delay time.

The method of any of the preceding paragraphs and/or any of the methods disclosed herein can have one or more of the following features. Calculating the current network transmission delay time can include determining a difference between the timestamp and a time provided by a patient-side real-time clock, and the method can include synchronizing the patient-side real-time clock with a network based real-time clock using a network time protocol. Delivering the control signals can include synchronizing delivery of the control signals to a patient-side clock signal and further including selecting each successive control signal based on a closest match between the patient-side clock signal and the timestamp of the corresponding timestamped input signal. Generating the plurality of control signals can include generating each control signal by interpolating between at least two successive input signals to produce a control signal approximating a position of one or more hand controllers of the surgeon input console at a time between the timestamps associated with the at least two successive input signals. The robotic surgery system can generate event-oriented notifications at the patient-side location, and the method can include associating each event-oriented notification to generate a notification record. The notification record can include: a timestamp indicating a time at which the event-oriented notification was generated; status information including information indicating a processing status of the event-oriented notification; timeout information including information indicating an expiry time by which the event-oriented notification should be processed; and transmitting each notification record to the surgeon-side location.

The method of any of the preceding paragraphs and/or any of the methods disclosed herein can have one or more of the following features. The method can include, at the surgeon-side location, receiving each notification record and accumulating the notification records for processing; for each notification record, when the status indicates that the notification record has not yet been communicated to the surgeon input console and the expiry time in the timeout information exceeds a current time at the surgeon-side location, causing an alert to be generated; and for each notification record, when the status indicates that the notification record has not yet been communicated to the surgeon input console and the expiry time in the timeout information does not exceed the current time at the surgeon-side location, causing a notification message to be communicated to the surgeon input console and changing the status in the notification record to indicate that the notification record has been processed.

A surgeon-side apparatus for remotely controlling a robotic surgery system located at a patient-side location can include: a surgeon-side interface processing circuitry configured to receive a plurality of input signals from a surgeon input console disposed at a surgeon-side location remote from the patient-side location; wherein the surgeon-side processing circuitry can be configured to: associate each input signal with a timestamp to generate a timestamped input signal, the timestamp indicating a time at which the input signal was received; and transmit the timestamped input signals over a network to the patient-side location to facilitate generation of a plurality of control signals for controlling operations of the robotic surgery system, each control signal being based on one or more timestamped input signals.

A system for controlling a robotic surgery system located at a patient-side location can include: a patient-side processing circuitry at the patient-side location, the patient-side processing circuitry being configured to receive a plurality of timestamped input signals from a surgeon-side processing circuitry and to generate a plurality of control signals for controlling operations of the robotic surgery system, each control signal being based on one or more timestamped input signals, and the patient-side processing circuitry can be configured to deliver the control signals to the robotic surgery system at successive times based on the timestamp of the respective one or more timestamped input signals.

A system for remotely controlling a robotic surgery system located at a patient-side location can include: a surgeon-side interface processing circuitry configured to receive a plurality of input signals from a surgeon input console disposed at a surgeon-side location remote from the patient-side location; a surgeon-side communications controller in communication with a plurality of available networks connecting between the surgeon-side location and the patient-side location, the surgeon-side communications controller being configured to make a selection of one or more selected networks from the plurality of available networks for transmission of the plurality of input signals to the patient-side location to facilitate generation of a plurality of control signals for controlling operations of the robotic surgery system.

The system of any of the preceding paragraphs and/or any of the systems disclosed herein can have one or more of the following features. The surgeon-side communications controller can be configured to make the selection is based on performance information obtained for the plurality of available networks. The performance information can be obtained from a performance management server in communication with the surgeon-side communications controller via one or more of the plurality of available networks. The surgeon-side communications controller can be configured to make a selection of a primary network and a secondary network from the plurality of available networks based on the performance information, and the surgeon-side communications controller can be configured to transmit input messages on the secondary network in the event of a transmission failure on the primary network.

The system of any of the preceding paragraphs and/or any of the systems disclosed herein can have one or more of the following features. The surgeon-side communications controller can be configured to make a selection of a primary network and a secondary network from the plurality of available networks based on the performance information, and wherein the surgeon-side communications controller can be configured to transmit input messages on both the primary and the secondary network. The surgeon-side communications controller can be further configured to transmit event-oriented notifications and wherein the surgeon-side communications controller can be configured to make a selection of a primary network and a secondary network from the plurality of available networks based on the performance information and to transmit input messages on the primary network and the event-oriented notifications on the secondary network. The input signals can include at least some input signals that are considered critical input signals, and wherein the surgeon-side controller can be configured to transmit event-oriented signals on an available network that has a highest level of performance based on the performance information.

The system of any of the preceding paragraphs and/or any of the systems disclosed herein can have one or more of the following features. The surgeon-side controller can be configured to transmit the critical input signals on at least one other available network. The surgeon-side controller can be configured to inhibit controlling of the robotic surgery system when the plurality of available networks do not meet a performance criterion. The surgeon-side communications controller can be configured to make a selection of at least a primary network and a secondary network from the plurality of available networks and to cause some of input messages to be transmitted on the primary network and other input messages to be transmitted on the secondary network.

The system of any of the preceding paragraphs and/or any of the systems disclosed herein can have one or more of the following features. The plurality of available networks can include one or more of: an internet network; a broadband enterprise network; a cellular radio network; a fiber optic network; or a satellite-based network.

The system of any of the preceding paragraphs and/or any of the systems disclosed herein can have one or more of the following features. The system can include, at the patient-side location: a patient-side communications controller in communication with the plurality of available networks, the communications controller being configured to receive input signals transmitted over the one or more selected networks to the patient-side location and to process the received input signals to generate an input signal stream; a patient-side processing circuitry in communication with the patient-side communications controller for receiving the input signal stream, the patient-side processing circuitry being configured to generate the plurality of control signals based on input signals in the input signal stream and to deliver the control signals to the robotic surgery system.

The system of any of the preceding paragraphs and/or any of the systems disclosed herein can have one or more of the following features. The patient-side communications controller can be configured to generate the input signal stream by determining whether an input signal received over one of the selected networks has been previously received over another of the selected networks and discarding a later received input signal. The surgeon-side communications controller or patient-side communications controller can be implemented as a software-defined wide area network (SD-WAN).

The system of any of the preceding paragraphs and/or any of the systems disclosed herein can have one or more of the following features. The system can include an in-patient imaging system located at the patient-side location, the in-patient imaging system configured to generate a plurality of image frames and wherein: the patient-side processing circuitry is operably configured to encode the image frames into an image data stream; the patient-side communications controller can be configured to make a selection of one or more selected networks from the plurality of available networks for transmission of the image data stream to the patient-side location to facilitate display of the in-patient image frames at the surgeon-side location.

A method for operating a robotic surgery system located at a patient-side location from a remotely located surgeon-side location can include: generating a plurality of image frames of a surgical site from an in-patient imaging system located at the patient-side location; receiving the plurality of image frames at a video encoder implemented at least in part using hardware circuitry; causing the video encoder to encode the plurality of image frames into an image data stream for transmission over a network to the surgeon-side location for display at the surgeon-side location.

The method of any of the preceding paragraphs and/or any of the methods disclosed herein can have one or more of the following features. The method can include, at the surgeon-side location: receiving the image data stream at a video decoder implemented at least in part using hardware circuitry and causing the video encoder to decode the image data stream to generate a plurality of image frames for display. The hardware circuitry of the video encoder can include circuitry implemented using one or more integrated circuit device. The integrated circuit device can include a configurable integrated circuit device including at least one of a field-programmable gate array (FPGA) or an application-specific integrated circuit (ASIC). The hardware circuitry can include a graphics processing unit (GPU), and wherein the video encoder can be implemented using a software codec that can be configured to be executed at least in part by the GPU.

A system for remotely controlling robotic surgery can include: a patient-side hardware circuitry configured to be integrated with a patient-side robotic surgery system that includes at least one surgical instrument configured manipulate tissue of a patient and at least one imaging system configured to facilitate manipulation of tissue of the patient and a surgeon-side hardware circuitry configured to be located remotely from the patient-side robotic surgery system and be integrated with a surgeon console that includes one or more input devices for controlling the at least one surgical instrument and the at least one imaging system of the patient-side robotic surgery system. The surgeon-side hardware circuitry can be configured to: receive from the surgeon console an input signal for controlling movement or actuation of the at least one surgical instrument or the at least one imaging system, the input signal being generated as a result of a surgeon physically interacting with the one or more input devices of the surgeon console, and the input signal indicating a desired movement of the at least one surgical instrument or at least one imaging system in a workspace associated with the surgeon console; associate the input signal with an indication signifying a temporal order of the input signal; group the input signal and the indication along with at least one other input signal and at least one other indication signifying the temporal order of the at least one other input signal; determine that a transmission criterion is satisfied; and in response to determining that the transmission criterion is satisfied, transmit over a network to the patient-side hardware circuitry a plurality of input signals that have been grouped together and a plurality of indications signifying the temporal order of the plurality of input signals, the plurality of input signals including the input signal and the at least one other input signal and the plurality of indications including the indication and the at least one other indication. The patient-side hardware circuitry can be configured to: receive over the network the plurality of input signals and the plurality of indications; chronologically order the plurality of input signals according to the plurality of indications; and provide the plurality of input signals arranged in a chronological order to the patient-side robotic surgery system and cause the patient-side robotic surgery system to control movement or actuation of the at least one surgical instrument or the at least one imaging system.

The system of any of the preceding paragraphs and/or any of the systems disclosed herein can have one or more of the following features. The surgeon-side hardware circuitry can be configured to not transmit any actuator drive signals for actuating the at least one surgical instrument or at least one imaging system. The indication signifying the temporal order of the input signal can include a first timestamp, and the at least one other indication signifying the temporal order of the at least one other input signal can include a second timestamp. Associating the input signal with the indication can include associating the input signal with the first timestamp corresponding to a time at which the input signal is received from the surgeon console. The patient-side hardware circuitry can be configured to discard the input signal in response to a determination that the first timestamp does not satisfy a transmission delay threshold.

The system of any of the preceding paragraphs and/or any of the systems disclosed herein can have one or more of the following features. The patient-side hardware circuitry can be configured to provide at least one input signal of the plurality of input signals to the patient-side robotic surgery system multiple times to satisfy a threshold input signal rate of the patient-side robotic surgery system. The patient-side hardware circuitry can be configured to provide the at least one input signal to the patient-side robotic surgery system multiple times in response to a rate of receiving the plurality of input signals not satisfying the threshold input signal rate.

The system of any of the preceding paragraphs and/or any of the systems disclosed herein can have one or more of the following features. The transmission criterion can include grouping a threshold number of input signals for transmission over the network to the patient-side hardware circuitry. The surgeon-side hardware circuitry can be configured to select the network from a plurality of available networks in response to performance characteristics of the network exceeding performance characteristics of any other network in the plurality of available networks.

The system of any of the preceding paragraphs and/or any of the systems disclosed herein can have one or more of the following features. The patient-side hardware circuitry can be configured to: receive a plurality of image frames of a surgical site captured by the at least one imaging system; encode the plurality of image frames into an image data stream for transmission over the network, a size of the image data stream being smaller than an aggregate size of the plurality of image frames; and transmit the image data stream over the network. The surgeon-side hardware circuitry can be configured to: receive the image data stream over the network; decode the image data stream into the plurality of image frames; and provide the plurality of image frames to the surgeon console for being displayed on a display. The patient-side hardware circuitry can be configured to encode the plurality of image frames with a circuitry that implements a hardware codec.

A system for remotely controlling robotic surgery can include a patient-side hardware circuitry configured to be integrated with a patient-side robotic surgery system that includes at least one surgical instrument configured manipulate tissue of a patient and at least one imaging system configured to facilitate manipulation of tissue of the patient and a surgeon-side hardware circuitry configured to be located remotely from the patient-side robotic surgery system and be integrated with a surgeon console that includes one or more input devices for controlling the at least one surgical instrument and the at least one imaging system of the patient-side robotic surgery system. The surgeon-side hardware circuitry can be configured to: receive from the surgeon console a plurality of input signals for controlling movement or actuation of the at least one surgical instrument or the at least one imaging system, the plurality of input signals being generated as a result of a surgeon physically interacting with the one or more input devices of the surgeon console, and the plurality of input signals indicating desired movements of the at least one surgical instrument or at least one imaging system in a workspace associated with the surgeon console and select a subset of the plurality of input signals and transmit the subset of the plurality of input signals over a network to the patient-side hardware circuitry to cause movement or actuation of the at least one surgical instrument or the at least one imaging system. The patient-side hardware circuitry can be configured to: receive over the network the subset of the plurality of input signals and provide the subset of the plurality of input signals to the patient-side robotic surgery system and cause the patient-side robotic surgery system to control movement or actuation of the at least one surgical instrument or the at least one imaging system.

The system of any of the preceding paragraphs and/or any of the systems disclosed herein can have one or more of the following features. The surgeon-side hardware circuitry can be configured to not transmit any actuator drive signals for actuating the at least one surgical instrument or at least one imaging system. The surgeon-side hardware circuitry can be configured to select the subset of the plurality of input signals by periodically sampling the plurality of input signals. A rate at which the surgeon-side hardware circuitry can be configured to periodically sample the plurality of input signals can match a rate at which the patient-side robotic surgery system can be configured to control movement or actuation of the at least one surgical instrument or the at least one imaging system.

The system of any of the preceding paragraphs and/or any of the systems disclosed herein can have one or more of the following features. The patient-side hardware circuitry can be configured to: interpolate between at least two input signals of the plurality of input signals to produce an estimated input signal approximating desired movements of the at least one surgical instrument or at least one imaging system in a time interval delineated by times of occurrence of the at least two input signals and provide the estimated input signal to the patient-side robotic surgery system and cause the patient-side robotic surgery system to control movement or actuation of the at least one surgical instrument or the at least one imaging system.

The system of any of the preceding paragraphs and/or any of the systems disclosed herein can have one or more of the following features. The patient-side hardware circuitry can be configured to: generate a notification record that includes status information indicating a processing status of an event-oriented notification generated by the patient-side robotic surgery system and timeout information indicating an expiry time by which the event-oriented notification should be processed; and transmit the notification record over the network to the surgeon-side hardware circuitry. The surgeon-side hardware circuitry can be configured to: receive the notification record over the network; in response to the processing status indicating that the notification record has not yet been communicated to the surgeon console and the expiry time not exceeding a current time of the surgeon-side hardware circuitry, communicate the event-oriented notification to the surgeon console and change the processing status in the notification record to indicate that the notification record has been processed; and in response to the processing status indicating that the notification record has not yet been communicated to the surgeon console and the expiry time exceeding the current time of the surgeon-side hardware circuitry, generate an alert.

The system of any of the preceding paragraphs and/or any of the systems disclosed herein can have one or more of the following features. The patient-side hardware circuitry can be configured to: receive a plurality of image frames of a surgical site captured by the at least one imaging system; encode the plurality of image frames into an image data stream for transmission over the network, a size of the image data stream being smaller than an aggregate size of the plurality of image frames; and transmit the image data stream over the network. The surgeon-side hardware circuitry can be configured to: receive the image data stream over the network; decode the image data stream into the plurality of image frames; and provide the plurality of image frames to the surgeon console for being displayed on a display. The patient-side hardware circuitry can be configured to encode the plurality of image frames with a circuitry that implements a hardware codec.

The system of any of the preceding paragraphs and/or any of the systems disclosed herein can have one or more of the following features. The subset of the plurality of input signals can be selected to not exceed a threshold rate of transmission across the network.

A system for remotely controlling robotic surgery can include a first non-transitory computer readable medium storing first instructions that, when executed by one or more first processors configured to 1) be located remotely from a patient-side robotic surgery system that includes at least one surgical instrument configured manipulate tissue of a patient and at least one imaging system configured to facilitate manipulation of tissue of the patient and 2) be integrated with a surgeon console that includes one or more input devices for controlling the at least one surgical instrument and the at least one imaging system of the patient-side robotic surgery system, cause the one or more first processors to: receive from the surgeon console an input signal for controlling movement or actuation of the at least one surgical instrument or the at least one imaging system, the input signal being generated as a result of a surgeon physically interacting with the one or more input devices of the surgeon console, and the input signal indicating a desired movement of the at least one surgical instrument or at least one imaging system in a workspace associated with the surgeon console; associate the input signal with an indication signifying a temporal order of the input signal; group the input signal and the indication along with at least one other input signal and at least one other indication signifying the temporal order of the at least one other input signal; determine that a transmission criterion is satisfied; and in response determining that the transmission criterion is satisfied, transmit over a network a plurality of input signals that have been grouped together and a plurality of indications signifying the temporal order of the plurality of input signals, the plurality of input signals including the input signal and the at least one other input signal and the plurality of indications including the indication and the at least one other indication. The system can include a second non-transitory computer readable medium storing second instructions that, when executed by one or more second processors integrated with the patient-side robotic surgery system, cause the one or more second processors to: receive over the network the plurality of input signals and the plurality of indications; chronologically order the plurality of input signals according to the plurality of indications; and provide the plurality of input signals arranged in a chronological order to the patient-side robotic surgery system and cause the patient-side robotic surgery system to control movement or actuation of the at least one surgical instrument or the at least one imaging system.

The system of any of the preceding paragraphs and/or any of the systems disclosed herein can have one or more of the following features. The second instructions can cause the one or more second processors to: generate a notification record that includes status information indicating a processing status of an event-oriented notification generated by the patient-side robotic surgery system and timeout information indicating an expiry time by which the event-oriented notification should be processed; and transmit the notification record over the network. The first instructions can cause the one or more first processors to: receive the notification record over the network; in response to the processing status indicating that the notification record has not yet been communicated to the surgeon console and the expiry time not exceeding a current time of the one or more first processors, communicate the event-oriented notification to the surgeon console and change the processing status in the notification record to indicate that the notification record has been processed; and in response to the processing status indicating that the notification record has not yet been communicated to the surgeon console and the expiry time exceeding the current time of the one or more first processors, generate an alert.

The system of any of the preceding paragraphs and/or any of the systems disclosed herein can have one or more of the following features. The second instructions can cause the one or more second processors to: interpolate between at least two input signals of the plurality of input signals to produce an estimated input signal approximating desired movements of the at least one surgical instrument or at least one imaging system in a time interval delineated by times of occurrence of the at least two input signals; and provide the estimated input signal to the patient-side robotic surgery system and cause the patient-side robotic surgery system to control movement or actuation of the at least one surgical instrument or the at least one imaging system.

The system of any of the preceding paragraphs and/or any of the systems disclosed herein can have one or more of the following features. The first instructions can cause the one or more first processors to not transmit any actuator drive signals for actuating the at least one surgical instrument or at least one imaging system.

The system of any of the preceding paragraphs and/or any of the systems disclosed herein can have one or more of the following features. The second instructions can cause the one or more second processors to: receive a plurality of image frames of a surgical site captured by the at least one imaging system; encode the plurality of image frames into an image data stream for transmission over the network, a size of the image data stream being smaller than an aggregate size of the plurality of image frames; and transmit the image data stream over the network. The first instructions can cause the one or more first processors to: receive the image data stream over the network; decode the image data stream into the plurality of image frames; and provide the plurality of image frames to the surgeon console for being displayed on a display.

A system for remotely controlling robotic surgery includes: a patient-side hardware circuitry configured to be integrated with a patient-side robotic surgery system that includes at least one surgical instrument configured manipulate tissue of a patient and at least one imaging system configured to facilitate manipulation of tissue of the patient, the at least one surgical instrument including an energy delivery instrument configured deliver energy to cut tissue of the patient; and a surgeon-side hardware circuitry configured to be located remotely from the patient-side robotic surgery system and be integrated with a surgeon console that includes one or more input devices for controlling the at least one surgical instrument and the at least one imaging system of the patient-side robotic surgery system. The surgeon-side hardware circuitry can be configured to: receive from the surgeon console a plurality of indications for controlling the at least one surgical instrument or the at least one imaging system, the plurality of indications being generated as a result of a surgeon physically interacting with the one or more input devices of the surgeon console, the plurality of indications signifying desired movements and actuations of the at least one surgical instrument or at least one imaging system in a workspace associated with the surgeon console, and the plurality of indications including a first indication for activating the energy delivery instrument and a second indication for deactivating the energy delivery instrument; select at least one first network from a plurality of available networks for transmission of the first and second indications to the patient-side hardware circuitry to control the energy delivery instrument, the at least one first network having performance characteristics that exceed performance characteristics of any other network in the plurality of available networks, wherein selection of the at least one first network facilitates timely delivery of the first and second indications to the patient-side hardware circuitry such that safety of the patient is not compromised; transmit the first indication over the at least one first network to the patient-side hardware circuitry to control the energy delivery instrument; determine that performance characteristics of at least one second network of the plurality of available networks exceed performance characteristics of any other network in the plurality of available networks; in response to the determination that performance characteristics of the at least one second network of the plurality of available networks exceed performance characteristics of any other network in the plurality of available networks, select the at least one second network for transmission of the second indication to the patient-side hardware circuitry, wherein selection of the at least one second network ensures that the second indication is timely delivered to the patient-side hardware circuitry such that safety of the patient is not compromised; and transmit the second indication over the at least one second network to the patient-side hardware circuitry to control the energy delivery instrument. The patient-side hardware circuitry can be configured to: receive the first indication over the at least one first network, provide the first indication to the patient-side robotic surgery system, and cause the patient-side robotic surgery system to activate the energy delivery instrument; and receive the second indication over the at least one second network, provide the second indication to the patient-side robotic surgery system, and cause the patient-side robotic surgery system to deactivate the energy delivery instrument.

The system of any of the preceding paragraphs and/or any of the systems disclosed herein can have one or more of the following features. The energy delivery instrument can be a cautery instrument. The first indication can be a first signal and the second indication can be a second signal.

The system of any of the preceding paragraphs and/or any of the systems disclosed herein can have one or more of the following features. The patient-side hardware circuitry can be configured to, in response to not receiving the second indication from the surgeon-side hardware circuitry within a threshold duration of time following receipt of the first indication, generate a substitute second indication subsequent to expiration of the threshold duration of time; and provide the substitute second indication to the patient-side robotic surgery system and cause the patient-side robotic surgery system to deactivate the energy delivery instrument.

The system of any of the preceding paragraphs and/or any of the systems disclosed herein can have one or more of the following features. The surgeon-side hardware circuitry can be configured to: determine that performance characteristics of the at least one first network do not satisfy minimum performance criteria; and in response to the determination that performance characteristics of the at least one first network do not satisfy minimum performance criteria, inhibit transmission of the first indication to the patient-side hardware circuitry.

The system of any of the preceding paragraphs and/or any of the systems disclosed herein can have one or more of the following features. The surgeon-side hardware circuitry can be configured to select the at least one first network based on performance information of the plurality of available networks, the performance information being associated with performance characteristics of the plurality of available networks; and the performance information can be obtained from a performance management server in communication with the surgeon-side hardware circuitry via one or more of the plurality of available networks.

The system of any of the preceding paragraphs and/or any of the systems disclosed herein can have one or more of the following features. The surgeon-side hardware circuitry can be configured to: designate the at least one second network as a primary network and select a secondary network from the plurality of available networks based on the performance information; and transmit the second indication on the secondary network responsive to a transmission failure on the primary network.

The system of any of the preceding paragraphs and/or any of the systems disclosed herein can have one or more of the following features. The surgeon-side hardware circuitry can be configured to: designate the at least one second network as a primary network and select a secondary network from the plurality of available networks based on the performance information; and transmit the second indication on the primary and secondary networks.

The system of any of the preceding paragraphs and/or any of the systems disclosed herein can have one or more of the following features. Selection of the at least one first network or the at least one second network can be performed by using software-defined wide area network (SD-WAN) architecture.

A system for remotely controlling robotic surgery can include a patient-side hardware circuitry configured to be integrated with a patient-side robotic surgery system that includes at least one surgical instrument configured manipulate tissue of a patient and at least one imaging system configured to facilitate manipulation of tissue of the patient, the at least one surgical instrument including an energy delivery instrument configured deliver energy to cut tissue of the patient; and a surgeon-side hardware circuitry configured to be located remotely from the patient-side robotic surgery system and be integrated with a surgeon console that includes one or more input devices for controlling the at least one surgical instrument and the at least one imaging system of the patient-side robotic surgery system. The surgeon-side hardware circuitry can be configured to: receive from the surgeon console a plurality of indications for controlling the at least one surgical instrument or the at least one imaging system, the plurality of indications being generated as a result of a surgeon physically interacting with the one or more input devices of the surgeon console, the plurality of indications signifying desired movements and actuations of the at least one surgical instrument or at least one imaging system in a workspace associated with the surgeon console, and the plurality of indications including a first indication for activating the energy delivery instrument and a second indication for deactivating the energy delivery instrument; and transmit over at least two networks the first and second indications to the patient-side hardware circuitry to control the energy delivery instrument, wherein transmission over the at least two networks ensures that the second indication is timely delivered to the patient-side hardware circuitry such that safety of the patient is not compromised. The patient-side hardware circuitry can be configured to: receive a plurality of copies of the first indication over the at least two networks and select a single copy of the first indication from the plurality of copies of the first indication; receive a plurality of copies of the second indication over the at least two networks and select a single copy of the second indication from the plurality of copies of the second indication; provide the single copy of the first indication to the patient-side robotic surgery system and cause the patient-side robotic surgery system to activate the energy delivery instrument; and provide the single copy of the second indication to the patient-side robotic surgery system and cause the patient-side robotic surgery system to deactivate the energy delivery instrument.

The system of any of the preceding paragraphs and/or any of the systems disclosed herein can have one or more of the following features. The patient-side hardware circuitry can be configured to: select an earliest received copy of the first indication as the single copy of the first indication; and select an earliest received copy of the second indication as the single copy of the second indication.

The system of any of the preceding paragraphs and/or any of the systems disclosed herein can have one or more of the following features. The patient-side hardware circuitry can be configured to discard all other copies of the first and second indications. The surgeon-side hardware circuitry can be configured to select the at least two networks from a plurality of available networks in response to a determination that the at least two networks have performance characteristics that exceed performance characteristics of any other network in the plurality of available networks. Selection of the at least two networks can be performed by using software-defined wide area network (SD-WAN) architecture.

The system of any of the preceding paragraphs and/or any of the systems disclosed herein can have one or more of the following features. The surgeon-side hardware circuitry can be configured to: determine that another network from a plurality of available networks exceeds performance characteristics of a first network of the at least two networks; and in response to the determination that another network exceeds performance characteristics of the first network of the at least two networks, replace the first network with another network in the at least two networks. The surgeon-side hardware circuitry can be configured to replace the first network with another network in the at least two networks subsequent to transmission of the first indication but prior to transmission of the second indication.

The system of any of the preceding paragraphs and/or any of the systems disclosed herein can have one or more of the following features. Tthe surgeon-side hardware circuitry can be configured to: determine that there are no two or more networks that satisfy minimum performance criteria in a plurality of available networks; and in response to the determination that there are no two or more networks that satisfy minimum performance criteria in the plurality of available networks, prevent transmission of the first and second indications to the patient-side hardware circuitry.

The system of any of the preceding paragraphs and/or any of the systems disclosed herein can have one or more of the following features. The first indication can be a first signal and the second indication can be a second signal. The at least two networks can include one or more networks that guarantee performance under a service level agreement (SLA).

A system for remotely controlling robotic surgery can include: a first non-transitory computer readable medium storing first instructions that, when executed by one or more first processors configured to 1) be located remotely from a patient-side robotic surgery system that includes at least one surgical instrument configured to manipulate tissue of a patient and at least one imaging system configured to facilitate manipulation of tissue of the patient, the at least one surgical instrument including an energy delivery instrument configured deliver energy to cut tissue of the patient and 2) be integrated with a surgeon console that includes one or more input devices for controlling the at least one surgical instrument and the at least one imaging system of the patient-side robotic surgery system, cause the one or more first processors to: receive from the surgeon console a plurality of indications for controlling the at least one surgical instrument or the at least one imaging system, the plurality of indications being generated as a result of a surgeon physically interacting with the one or more input devices of the surgeon console, the plurality of indications signifying desired movements and actuations of the at least one surgical instrument or at least one imaging system in a workspace associated with the surgeon console, and the plurality of indications including a first indication for activating the energy delivery instrument and a second indication for deactivating the energy delivery instrument; and transmit over at least two networks the first and second indications to control the energy delivery instrument, wherein transmission over the at least two networks ensures that the second indication is timely delivered to the patient-side robotic surgery system such that safety of the patient is not compromised. The system can include a second non-transitory computer readable medium storing second instructions that, when executed by one or more second processors integrated with the patient-side robotic surgery system, cause the one or more second processors to: receive a plurality of copies of the first indication over the at least two networks and select a single copy of the first indication from the plurality of copies of the first indication; receive a plurality of copies of the second indication over the at least two networks and select a single copy of the second indication from the plurality of copies of the second indication; provide the single copy of the first indication to the patient-side robotic surgery system and cause the patient-side robotic surgery system to activate the energy delivery instrument; and provide the single copy of the second indication to the patient-side robotic surgery system and cause the patient-side robotic surgery system to deactivate the energy delivery instrument.

The system of any of the preceding paragraphs and/or any of the systems disclosed herein can have one or more of the following features. The second instructions can cause the one or more second processors to: select an earliest received copy of the first indication as the single copy of the first indication; and select an earliest received copy of the second indication as the single copy of the second indication.

The system of any of the preceding paragraphs and/or any of the systems disclosed herein can have one or more of the following features. The first instructions can cause the one or more first processors to select the at least two networks from a plurality of available networks in response to a determination that the at least two networks have performance characteristics that exceed performance characteristics of any other network in the plurality of available networks.

The system of any of the preceding paragraphs and/or any of the systems disclosed herein can have one or more of the following features. The first instructions can cause the one or more first processors to: determine that another network from a plurality of available networks exceeds performance characteristics of a first network of the at least two networks; and in response to the determination that another network exceeds performance characteristics of the first network of the at least two networks, replace the first network with another network in the at least two networks.

The system of any of the preceding paragraphs and/or any of the systems disclosed herein can have one or more of the following features. The first instructions can cause the one or more first processors to replace the first network with another network in the at least two networks subsequent to transmission of the first indication but prior to transmission of the second indication.

The system of any of the preceding paragraphs and/or any of the systems disclosed herein can have one or more of the following features. The first instructions can cause the one or more first processors to: determine that there are no two or more networks that satisfy minimum performance criteria in a plurality of available networks; and in response to the determination that there are no two or more networks that satisfy minimum performance criteria in the plurality of available networks, prevent transmission of the first and second indications.

A system for remotely controlling robotic surgery can include a patient-side hardware circuitry configured to be integrated with a patient-side robotic surgery system that includes at least one surgical instrument configured manipulate tissue of a patient at a surgical site and at least one imaging system configured to facilitate manipulation of tissue of the patient. The patient-side hardware circuitry can be configured to: receive a plurality of image frames of the surgical site captured by the at least one imaging system; with a circuitry that implements a hardware codec, encode the plurality of image frames into an image data stream for transmission over at least one network, a size of the image data stream being smaller than an aggregate size of the plurality of image frames; and transmit the image data stream over the at least one network. The system can include a surgeon-side hardware circuitry configured to be located remotely from the patient-side robotic surgery system and be integrated with a surgeon console that includes one or more input devices for controlling the at least one surgical instrument and the at least one imaging system of the patient-side robotic surgery system and a display. the surgeon-side hardware circuitry can be configured to: receive the image data stream over the at least one network, decode the image data stream into the plurality of image frames, and provide the plurality of image frames to the surgeon console for being displayed on the display; receive from the surgeon console a plurality of input signals for controlling movement or actuation of the at least one surgical instrument or the at least one imaging system, the plurality of input signals being generated as a result of a surgeon physically interacting with the one or more input devices of the surgeon console based on viewing the plurality of image frames on the display, and the plurality of input signals indicating desired movements of the at least one surgical instrument or at least one imaging system in a workspace associated with the surgeon console; generate a plurality of indications signifying a temporal order of the plurality of input signals; and transmit the plurality of input signals along with the plurality of indications over the at least one network to the patient-side hardware circuitry to cause movement or actuation of the at least one surgical instrument or the at least one imaging system. The patient-side hardware circuitry can be configured to: receive over the at least one network the plurality of input signals and the plurality of indications; chronologically order the plurality of input signals according to the plurality of indications; and provide the plurality of input signals arranged in a chronological order to the patient-side robotic surgery system and cause the patient-side robotic surgery system to control movement or actuation of the at least one surgical instrument or the at least one imaging system.

The system of any of the preceding paragraphs and/or any of the systems disclosed herein can have one or more of the following features. The patient-side hardware circuitry can be configured to, with the circuitry that implements the hardware codec, encode a slice of at least one image frame of the plurality of image frames into the image data stream prior to an entirety of the at least one image frame having been received. The surgeon-side hardware circuitry can be configured to decode the image data stream into the plurality of image frames with a circuitry that implements the hardware codec. The surgeon-side hardware circuitry can be configured to select the at least one network from a plurality of available networks in response to performance characteristics of the at least one network exceeding performance characteristics of any other network in the plurality of available networks.

The system of any of the preceding paragraphs and/or any of the systems disclosed herein can have one or more of the following features. The patient-side hardware circuitry can be configured to: select at least two networks from a plurality of available networks in response to a determination that performance characteristics of the at least two networks exceed performance characteristics of any other network in a plurality of available networks; and transmit the image data stream over the at least two networks. The surgeon-side hardware circuitry can be configured to: receive a plurality of copies of the image data stream over the at least two networks; select a single copy of the image data stream from the plurality of copies of the image data stream; and decode the single copy of the image data stream into the plurality of image frames.

The system of any of the preceding paragraphs and/or any of the systems disclosed herein can have one or more of the following features. The surgeon-side hardware circuitry can be configured to select an earliest received copy of the image data stream as the single copy of the image data stream.

The system of any of the preceding paragraphs and/or any of the systems disclosed herein can have one or more of the following features. The plurality of indications signifying the temporal order of the plurality of input signals can include a plurality of timestamps.

A system for remotely controlling robotic surgery can include a patient-side hardware circuitry configured to be integrated with a patient-side robotic surgery system that includes at least one surgical instrument configured manipulate tissue of a patient at a surgical site and at least one imaging system configured to facilitate manipulation of tissue of the patient. The patient-side hardware circuitry can be configured to: receive a plurality of image frames of the surgical site captured by the at least one imaging system; encode the plurality of image frames into an image data stream, a size of the image data stream being smaller than an aggregate size of the plurality of image frames; select at least one first network from a plurality of networks, the at least one first network having performance characteristics that exceed performance characteristics of any other network in the plurality of networks; and transmit the image data stream over the at least one first network. The system can include a surgeon-side hardware circuitry configured to be located remotely from the patient-side robotic surgery system and be integrated with a surgeon console that includes one or more input devices for controlling the at least one surgical instrument and the at least one imaging system of the patient-side robotic surgery system and a display. The surgeon-side hardware circuitry can be configured to: receive the image data stream over the at least one first network, decode the image data stream into the plurality of image frames, and provide the plurality of image frames to the surgeon console for being displayed on the display; receive from the surgeon console a plurality of input signals for controlling movement or actuation of the at least one surgical instrument or the at least one imaging system, the plurality of input signals being generated as a result of a surgeon physically interacting with the one or more input devices of the surgeon console based on viewing the plurality of image frames on the display, and the plurality of input signals indicating desired movements of the at least one surgical instrument or at least one imaging system in a workspace associated with the surgeon console; generate a plurality of indications signifying a temporal order of the plurality of input signals; determine that performance characteristics of at least one second network of the plurality of networks exceed performance characteristics of any other network in the plurality of networks; in response to determining that performance characteristics of the at least one second network of the plurality of networks exceed performance characteristics of any other network in the plurality of networks, select the at least one second network for transmission of the plurality of input signals and the plurality of indications; and transmit the plurality of input signals along with the plurality of indications over the at least one second network to the patient-side hardware circuitry to cause movement or actuation of the at least one surgical instrument or the at least one imaging system. The patient-side hardware circuitry can be configured to: receive over the at least one second network the plurality of input signals and the plurality of indications; chronologically order the plurality of input signals according to the plurality of indications; and provide the plurality of input signals arranged in a chronological order to the patient-side robotic surgery system and cause the patient-side robotic surgery system to control movement or actuation of the at least one surgical instrument or the at least one imaging system.

The system of any of the preceding paragraphs and/or any of the systems disclosed herein can have one or more of the following features. The patient-side hardware circuitry can be configured to encode the image data stream into the plurality of image frames with a circuitry that implements a hardware codec. The surgeon-side hardware circuitry can be configured to decode the image data stream into the plurality of image frames with a circuitry that implements the hardware codec. The patient-side hardware circuitry can be configured to encode a slice of at least one image frame of the plurality of image frames into the image data stream prior to an entirety of the at least one image frame having been received. Selection of the at least one first network or the at least one second network can be performed by using software-defined wide area network (SD-WAN) architecture.

The system of any of the preceding paragraphs and/or any of the systems disclosed herein can have one or more of the following features. The surgeon-side hardware circuitry can be configured to: determine that performance characteristics of the at least one second network do not satisfy minimum performance criteria; and in response to determining that performance characteristics of the at least one first network do not satisfy minimum performance criteria, inhibit transmission of at least some input signals of the plurality of input signals to the patient-side hardware circuitry. At least some input signals can be configured to cause the at least one surgical instrument to cut tissue of the patient.

A system for remotely controlling robotic surgery can include a patient-side hardware circuitry configured to be integrated with a patient-side robotic surgery system that includes at least one surgical instrument configured manipulate tissue of a patient at a surgical site and at least one imaging system configured to facilitate manipulation of tissue of the patient. The patient-side hardware circuitry can be configured to: receive a plurality of image frames of the surgical site captured by the at least one imaging system; encode the plurality of image frames into an image data stream, a size of the image data stream being smaller than an aggregate size of the plurality of image frames; and transmit the image data stream over at least one first network of a plurality of available networks. The system can include a surgeon-side hardware circuitry configured to be located remotely from the patient-side robotic surgery system and be integrated with a surgeon console that includes one or more input devices for controlling the at least one surgical instrument and the at least one imaging system of the patient-side robotic surgery system and a display. The surgeon-side hardware circuitry can be configured to: receive the image data stream over the at least one first network, decode the image data stream into the plurality of image frames, and provide the plurality of image frames to the surgeon console for being displayed on the display; receive from the surgeon console a plurality of input signals for controlling movement or actuation of the at least one surgical instrument or the at least one imaging system, the plurality of input signals being generated as a result of a surgeon physically interacting with the one or more input devices of the surgeon console based on viewing the plurality of image frames on the display, and the plurality of input signals indicating desired movements of the at least one surgical instrument or at least one imaging system in a workspace associated with the surgeon console; generate a plurality of indications signifying a temporal order of the plurality of input signals; select at least two second networks from the plurality of available networks for transmission of the plurality of input signals and the plurality of indications; and transmit the plurality of input signals along with the plurality of indications over the at least two second networks to the patient-side hardware circuitry to cause movement or actuation of the at least one surgical instrument or the at least one imaging system. The patient-side hardware circuitry can be configured to: receive over the at least two second networks the plurality of input signals and the plurality of indications; chronologically order the plurality of input signals according to the plurality of indications; and provide the plurality of input signals arranged in a chronological order to the patient-side robotic surgery system and cause the patient-side robotic surgery system to control movement or actuation of the at least one surgical instrument or the at least one imaging system.

The system of any of the preceding paragraphs and/or any of the systems disclosed herein can have one or more of the following features. The surgeon-side hardware circuitry can be configured to select the at least two second networks from the plurality of available networks in response to a determination that the at least two second networks have performance characteristics that exceed performance characteristics of any other network in the plurality of available networks. The surgeon-side hardware circuitry can be configured to select the at least one first network as one of the at least two second networks.

The system of any of the preceding paragraphs and/or any of the systems disclosed herein can have one or more of the following features. At least one first network can include at least two first networks, and the surgeon-side hardware circuitry can be configured to: receive a plurality of copies of the image data stream over the at least two first networks; select a single copy of the image data stream from the plurality of copies of the image data stream; and decode the single copy of the image data stream into the plurality of image frames.

The system of any of the preceding paragraphs and/or any of the systems disclosed herein can have one or more of the following features. The patient-side hardware circuitry can be configured to: receive a plurality of copies of an input signal from the plurality of input signals over the at least two second networks; and select a single copy of the input signal from the plurality of copies of the input signal for chronologically ordering the plurality of input signals according to the plurality of indications. The patient-side hardware circuitry can be configured to select an earliest received copy of the input signal as the single copy of the input signal.

The system of any of the preceding paragraphs and/or any of the systems disclosed herein can have one or more of the following features. The patient-side hardware circuitry can be configured to encode the image data stream into the plurality of image frames with a circuitry that implements a hardware codec; and the surgeon-side hardware circuitry can be configured to decode the image data stream into the plurality of image frames with a circuitry that implements the hardware codec. Selection of the at least two second networks can be performed by using software-defined wide area network (SD-WAN) architecture.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, implementation, or example are to be understood to be applicable to any other aspect, implementation, or example described herein unless incompatible therewith. All of the features disclosed in this specification (including any accompanying claims, abstract and drawings), and/or all of the steps of any method or process so disclosed, can be combined in any combination, except combinations where at least some of such features and/or steps are mutually exclusive. The protection is not restricted to the details of any foregoing implementations. The protection extends to any novel one, or any novel combination, of the features disclosed in this specification (including any accompanying claims, abstract and drawings), or to any novel one, or any novel combination, of the steps of any method or process so disclosed.

While certain implementations have been described, these implementations have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some cases, the actual steps taken in the processes illustrated and/or disclosed may differ from those shown in the figures. Depending on the implementation, certain of the steps described above may be removed, others may be added. For example, the actual steps and/or order of steps taken in the disclosed processes may differ from those shown in the figure. Various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific examples disclosed above may be combined in different ways to form additional implementations, all of which fall within the scope of the present disclosure.

Conditional language used herein, such as, among others, "can," "could", "might," "may", "e.g.," and the like, unless specifically stated otherwise, or otherwise understood within the context as used, is generally intended to convey that certain implementation include, while other implementations do not include, certain features, elements and/or states. Thus, such conditional language is not generally intended to imply that features, elements and/or states are in any way required for one or more implementations or that one or more implementations necessarily include logic for deciding, with or without author input or prompting, whether these features, elements and/or states are included or are to be performed in any particular implementation. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain implementations require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, or within less than 0.01% of the stated value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

While specific implementations have been described and illustrated, such implementations should be considered illustrative only and not as limiting. Accordingly, the scope of the present disclosure is not intended to be limited by the specific disclosures of preferred implementations herein, and may be defined by claims as presented herein or as presented in the future.

What is claimed is:

1. A system for remotely controlling robotic surgery, the system comprising:
   a patient-side hardware circuitry configured to be integrated with a patient-side robotic surgery system that includes at least one surgical instrument configured to manipulate tissue of a patient and at least one imaging system configured to facilitate manipulation of tissue of the patient; and
   a surgeon-side hardware circuitry configured to be located remotely from the patient-side robotic surgery system and be integrated with a surgeon console that includes one or more input devices for controlling the at least one surgical instrument and the at least one imaging system of the patient-side robotic surgery system, the surgeon-side hardware circuitry being further configured to:
      receive from the surgeon console an input signal for controlling movement or actuation of the at least one surgical instrument or the at least one imaging system, the input signal being generated as a result of a surgeon physically interacting with the one or more input devices of the surgeon console, and the input signal indicating a desired movement of the at least one surgical instrument or at least one imaging system in a workspace associated with the surgeon console;
      associate the input signal with an indication signifying a temporal order of the input signal;
      group the input signal and the indication along with at least one other input signal and at least one other indication signifying the temporal order of the at least one other input signal;
      determine that a transmission criterion is satisfied; and
      in response to determining that the transmission criterion is satisfied, transmit over a network to the patient-side hardware circuitry a plurality of input signals that have been grouped together and a plurality of indications signifying the temporal order of the plurality of input signals, the plurality of input signals including the input signal and the at least one other input signal and the plurality of indications including the indication and the at least one other indication,
   the patient-side hardware circuitry being further configured to:
      receive over the network the plurality of input signals and the plurality of indications;
      chronologically order the plurality of input signals according to the plurality of indications; and
      provide the plurality of input signals arranged in a chronological order to the patient-side robotic surgery system and cause the patient-side robotic surgery system to control movement or actuation of the at least one surgical instrument or the at least one imaging system,
      wherein the patient-side hardware circuitry is further configured to provide an input signal of the plurality of input signals to the patient-side robotic surgery system multiple times to satisfy a threshold input signal rate of the patient-side robotic surgery system.

2. The system of claim 1, wherein the surgeon-side hardware circuitry is further configured to not transmit any actuator drive signals for actuating the at least one surgical instrument or at least one imaging system.

3. The system of claim 1, wherein the indication signifying the temporal order of the input signal comprises a first timestamp, and wherein the at least one other indication signifying the temporal order of the at least one other input signal comprises a second timestamp.

4. The system of claim 3, wherein associating the input signal with the indication comprises associating the input signal with the first timestamp corresponding to a time at which the input signal is received from the surgeon console.

5. The system of claim 3, wherein the patient-side hardware circuitry is configured to discard the input signal in response to a determination that the first timestamp does not satisfy a transmission delay threshold.

6. The system of claim 1, wherein the patient-side hardware circuitry is configured to provide the input signal to the patient-side robotic surgery system multiple times in response to a rate of receiving the plurality of input signals not satisfying the threshold input signal rate.

7. The system of claim 1, wherein the transmission criterion comprises grouping a threshold number of input signals for transmission over the network to the patient-side hardware circuitry.

8. The system of claim 1, wherein the surgeon-side hardware circuitry is configured to select the network from a plurality of available networks in response to performance characteristics of the network exceeding performance characteristics of any other network in the plurality of available networks.

9. The system of claim 1, wherein:
the patient-side hardware circuitry is further configured to:
receive a plurality of image frames of a surgical site captured by the at least one imaging system;
encode the plurality of image frames into an image data stream for transmission over the network, a size of the image data stream being smaller than an aggregate size of the plurality of image frames; and
transmit the image data stream over the network; and
the surgeon-side hardware circuitry is further configured to:
receive the image data stream over the network;
decode the image data stream into the plurality of image frames; and
provide the plurality of image frames to the surgeon console for being displayed on a display.

10. The system of claim 9, wherein the patient-side hardware circuitry is configured to encode the plurality of image frames with a circuitry that implements a hardware codec.

11. A system for remotely controlling robotic surgery, the system comprising:
a first non-transitory computer readable medium storing first instructions that, when executed by one or more first processors configured to 1) be located remotely from a patient-side robotic surgery system that includes at least one surgical instrument configured to manipulate tissue of a patient and at least one imaging system configured to facilitate manipulation of tissue of the patient and 2) be integrated with a surgeon console that includes one or more input devices for controlling the at least one surgical instrument and the at least one imaging system of the patient-side robotic surgery system, cause the one or more first processors to:
receive from the surgeon console an input signal for controlling movement or actuation of the at least one surgical instrument or the at least one imaging system, the input signal being generated as a result of a surgeon physically interacting with the one or more input devices of the surgeon console, and the input signal indicating a desired movement of the at least one surgical instrument or at least one imaging system in a workspace associated with the surgeon console;
associate the input signal with an indication signifying a temporal order of the input signal;
group the input signal and the indication along with at least one other input signal and at least one other indication signifying the temporal order of the at least one other input signal;
determine that a transmission criterion is satisfied; and
in response determining that the transmission criterion is satisfied, transmit over a network a plurality of input signals that have been grouped together and a plurality of indications signifying the temporal order of the plurality of input signals, the plurality of input signals including the input signal and the at least one other input signal and the plurality of indications including the indication and the at least one other indication; and
a second non-transitory computer readable medium storing second instructions that, when executed by one or more second processors integrated with the patient-side robotic surgery system, cause the one or more second processors to:
receive over the network the plurality of input signals and the plurality of indications;
chronologically order the plurality of input signals according to the plurality of indications; and
provide the plurality of input signals arranged in a chronological order to the patient-side robotic surgery system and cause the patient-side robotic surgery system to control movement or actuation of the at least one surgical instrument or the at least one imaging system,
wherein an input signal of the plurality of input signals is provided to the patient-side robotic surgery system multiple times to satisfy a threshold input signal rate of the patient-side robotic surgery system.

12. The system of claim 11, wherein:
the second instructions further cause the one or more second processors to:
generate a notification record comprising:
status information indicating a processing status of an event-oriented notification generated by the patient-side robotic surgery system; and
timeout information indicating an expiry time by which the event-oriented notification should be processed; and
transmit the notification record over the network; and
the first instructions further cause the one or more first processors to:
receive the notification record over the network;
in response to the processing status indicating that the notification record has not yet been communicated to the surgeon console and the expiry time not exceeding a current time of the one or more first processors, communicate the event-oriented notification to the surgeon console and change the processing status in the notification record to indicate that the notification record has been processed; and
in response to the processing status indicating that the notification record has not yet been communicated to the surgeon console and the expiry time exceeding the current time of the one or more first processors, generate an alert.

13. The system of claim 11, wherein the second instructions further cause the one or more second processors to:

interpolate between at least two input signals of the plurality of input signals to produce an estimated input signal approximating desired movements of the at least one surgical instrument or at least one imaging system in a time interval delineated by times of occurrence of the at least two input signals; and provide the estimated input signal to the patient-side robotic surgery system and cause the patient-side robotic surgery system to control movement or actuation of the at least one surgical instrument or the at least one imaging system.

14. The system of claim 11, wherein the first instructions further cause the one or more first processors to not transmit any actuator drive signals for actuating the at least one surgical instrument or at least one imaging system.

15. The system of claim 11, wherein:

the second instructions further cause the one or more second processors to:

receive a plurality of image frames of a surgical site captured by the at least one imaging system;

encode the plurality of image frames into an image data stream for transmission over the network, a size of the image data stream being smaller than an aggregate size of the plurality of image frames; and transmit the image data stream over the network; and the first instructions further cause the one or more first processors to:

receive the image data stream over the network;

decode the image data stream into the plurality of image frames; and provide the plurality of image frames to the surgeon console for being displayed on a display.

16. The system of claim 11, wherein the input signal is provided to the patient-side robotic surgery system multiple times in response to a rate of receiving the plurality of input signals not satisfying the threshold input signal rate.

* * * * *